US006143522A

United States Patent [19]
Helbing et al.

[11] Patent Number: 6,143,522
[45] Date of Patent: Nov. 7, 2000

[54] METHODS OF MODULATING APOPTOSIS

[75] Inventors: Caren C. Helbing; Karl Riabowol; Randall N. Johnston; Igor Garkavtsev, all of Calgary, Canada

[73] Assignee: University Technologies International, Inc., Calgary, Canada

[21] Appl. No.: 09/499,082

[22] Filed: Feb. 4, 2000

Related U.S. Application Data

[63] Continuation of application No. 08/828,158, Mar. 27, 1997, abandoned, which is a continuation-in-part of application No. 08/751,230, Nov. 15, 1996, which is a continuation-in-part of application No. 08/569,721, Dec. 8, 1995, Pat. No. 6,037,121.

[51] Int. Cl.$^7$ .............................. C12Q 1/68; C12N 15/11; C07H 21/04; C07K 5/00; C07K 14/00
[52] U.S. Cl. ................................ 435/69.1; 435/4; 435/6; 435/455; 536/231; 530/300; 530/350
[58] Field of Search ................................... 435/4, 6, 455, 435/69.1, 325; 536/23.1; 530/300, 350; 514/2, 44

[56] References Cited

U.S. PATENT DOCUMENTS

| 5,580,859 | 12/1996 | Felgner et al. ............................ 514/44 |
| 5,589,466 | 12/1996 | Felgner et al. ............................ 514/44 |

FOREIGN PATENT DOCUMENTS

| WO 90/02569 | 3/1990 | WIPO . |
| WO 92/00329 | 1/1992 | WIPO . |
| WO 95/15334 | 6/1995 | WIPO . |
| WO 95/19805 | 7/1995 | WIPO . |
| WO 95/21253 | 8/1995 | WIPO . |
| WO 95/23855 | 8/1995 | WIPO . |
| WO 95/25429 | 9/1995 | WIPO . |
| WO 97/21809 | 6/1997 | WIPO . |

OTHER PUBLICATIONS

Aharon, T. et al., "Selective Destabilization of Short–Lived mRNAs with the Granulocyte–Macrophage Colony–Stimulating Factor AU–Rich 3' Noncoding Region is Mediated by a Cotranslational Mechanism", *Mol. Cell. Biol.* 13:1971–1980 (1993).

Anderson, W. French, "Human gene therapy", *Science* 256:808–813 (May 1992).

Atadja, P. et al., "Increased activity of p53 in senescing fibroblasts" *Proc. Nat'l. Acad. Sci. USA* 92: 8348–8352 (1995).

Bond, et al., "Escape from senescence in human diploid fibroblasts induced directly by mutant p53" *Oncogene* 9:1885–1889 (1994).

Culver et al., "In Vivo gene transfer with retroviral vector–producer cells for treatment of experimental brain tumors", *Science* 256:1550–1552 (Jun. 1992).

Defeo–Jones, D., "Cloning of cDNAs for cellular proteins that bind to the retinoblastoma gene product", *Nature* 352:251–254 (1991).

Demetrick, D.J., "Fluorescence in situ hybridization and human cell cycle genes" In *the Cell Cycle—Materials and Methods* M. Pagano (ed.) Springer Verlag Press, 29–45 (1995).

El–Deiry, W.S. et al., "WAF1, a Potential Mediator of p53 Tumor Suppression", *Cell* 75:817–825 (1993).

Galli & Fratelli, "Activation of apoptosis by serum deprivation in a teratocarcinoma cell line: inhibition by L–acetycarnitine", *Exp. Cell Res.* 204:54–60 (1993).

Garkavtsev et al. (1996), "Suppression of the novel growth inhibitor p33$^{ING1}$ promotes neoplastic transformation", *Nature Genetics*, 14(4):415–420.

Garkavtsev et al. "The candidate tumor suppressor p33$^{ING1}$ cooperates with the p53 in cell growth control", *Nature* 391:295–298 (1998).

Gossen and Bujard, "Tight control of gene expression in mammalian cells by tetracycline–responsive promoters", *Proc. of Natl Acad. Sci.* 89(12):5547–5551 (1992).

Graessmann and Graessmann, "Microinjection of tissue culture cells", *Methods in Enzymology* 101:482–492 (1983).

Guan, K. et al., "Growth suppression by p18, a p16$^{INK4/MTS1}$ and p14$^{INK4B/MTS2}$–related CDK6 inhibitor, correlates with wild–type pRb function", *Genes & Dev.* 8:2939–2952 (1994).

Gudkov, A.V. et al., "Isolation of genetic suppressor elements, inducing resistance to topoisomerase II–interactive cytotoxic drugs, from human topoisomerase II cDNA", *Proc. Natl. Acad. Sc. USA* 90:3231–3235 (1993).

Gudkov, A. et al., "Cloning mammalian genes by expression selection of genetic suppressor elements: Associate of kinesin with drug resistance and cell immortalization" *Proc. Nat'l Acad. Sci. USA* 91:3744–3798 (1994).

Harper, J.W. et al., "The p21 Cdk–Interacting Protein Cip1 is a Potent Inhibitor of G1 Cyclin–Dependent Kinases", *Cell* 75:805–816 (1993).

Helbing, et al., "A novel candidate tumor suppressor, ING1, is involved in the regulation of apoptosis" *Cancer Research* 53:1255–1258 (1997).

Hillier et al., Database CST on MPSRcrhAccession No. T60958.

Hillier et al., (Feb. 1995), "Database EMBL Entry HS12525", *WashU–EST Project* .

Hunter, T. et al., "Cyclins and Cancer II: Cyclin D and CDK Inhibitors Come of Age", *Cell* 79:573–582 (1994).

Kamb, A. et al., "A Cell Cycle Regulator Potentially Involved in Genesis of Many Tumor Types", *Science* 264:436–440 (1994).

Kaneko, et al., "Adenovirus–mediated gene therapy of hepatocellular carcinoma using cancer–specific gene expression" *Cancer Research* 55:5283–5287 (1995).

(List continued on next page.)

Primary Examiner—Remy Yucel
Assistant Examiner—Sean McGarry
Attorney, Agent, or Firm—Burns Doane Swecker & Mathis L.L.P.

[57] ABSTRACT

The invention provides novel methods for modulating apoptosis in eukaryotic cells using peptides and proteins derived from p33$^{ING1}$ or oligonucleotides derived from the ING1 gene. The invention also provides method of determining the apoptotic characteristic of a eukaryotic cell.

11 Claims, 12 Drawing Sheets

OTHER PUBLICATIONS

Lee and Bernstein, "Apoptosis, cancer and the p53 tumor suppressor gene" *Cancer Met Rev.* 14:149–161 (1995).

Levine, A.J., "The Tumor Suppressor Genes", *Annu. Rev. Biochem.* 62:623–651 (1993).

Levine (1997), "p53, the Cellular Gatekeeper for Growth and Division", *Cell* 88:323–331.

Lisitsyn, N. et al., "Cloning the Differences Between Two Complex Genomes", *Science* 259:946–951 (1993).

Maestro et al., "Chromosome 13q deletion mapping in head and neck squamous cell carcinomas: identification of two distinct regions of preferential loss" *Cancer Research* 56:1146–1150 (1996).

Meikrantz and Schlegel, "Apoptosis and the cell cycle" *J. Cell Biochem* 58:160–174 (1995).

Miller, A.D. et al., "Improved Retroviral Vectors for Gene Transfer and Expression", *Biotechniques* 7:980–986 (1989).

Miller, Dusty A., "Human gene therapy comes of age" *Nature* 357:455–460 (Jun. 1992).

Mitelman et al., "Report of the committee on chromosome changes in neoplasia" *Cytogenet Cell Genet* 55:358–386 (1990).

Motomura et al., "Loss of alleles at loci on chromosome 13 in human primary gastric cancers" *Genomics* 2, 180–184 (1988).

Nobori, T. et al., "Deletions of the cyclin–dependent kinase–4 inhibitor gene in multiple human cancers", *Nature* 368:753–756 (1994).

Pear, W.S. et al., "Production of high titer helper–free retroviruses by transient transfection" *Proc. Natl. Acad. Sci.* 90:8392–8396 (1993).

Riabowol, K. et al., "The cdc2 Kinase Is a Nuclear Protein That Is Essential for Mitosis in Mammalian Cells", *Cell* 57:393–401 (1989).

Schneider E.L and Fowlkes, B.J., "Measurement of a DNA content and cell volume in senescent human fibroblasts utilizing flow miltiparameter single cell analysis" *Exp. Cell. Res.* 98:298–302 (1976).

Serrano, M. et al., "A new regulatory motif in cell–cycle control causing specific inhibition of cyclin D/CDK4", *Nature* 366:704–707 (1993).

Smith et al., "Antibodies to CD3/T–cell receptor complex induce death by apoptosis in immature T cells in thymic cultures", *Nature* 337:181–184 (1989).

Straus, D. et al., "Genomic subtraction for cloning DNA corresponding to deletion mutations", *Proc. Natl. Acad. Sc. USA* 87:1889–1893 (1990).

Thompson, M.E. et al., "Decreased expression of BRCA–1 accelerates growth and is often present during sporadic breast cancer progression" *Nature Genetics* 9:444–450 (1995).

Tsai, L.H. et al., "The cdk2 kinase is required for the G1– to –S transition in mammalian cells" *Oncogene* 8:1593–1602 (1993).

Weinberg, Robert A. (1991), "Tumor Suppressor Genes", *Science*, 254:1138–1146.

Wong, H. et al., "Monitoring mRNA expression by polymerase chain reaction: the "primer–dropping" method" *Anal. Biochem.* 223:251–258 (1994).

Xlong et al., (1993) "p21 is a Universal Inhibitor of Cyclin Kinases", *Nature* 366:701–704.

Yang, Y. et al., "An approach for treating the hepatobiliary disease of cystic fibrosis by somatic gene transfer" *Proc. Nat'l. Acad. Sci. USA* 90: 4061–4605 (1993).

Yaswen, P. et al., "Down–regulation of a calmodulin–related gene during transformation of human mammary epithelial cells", *Proc. Natl. Acad. Sc. USA* 87:7360–7364 (1990).

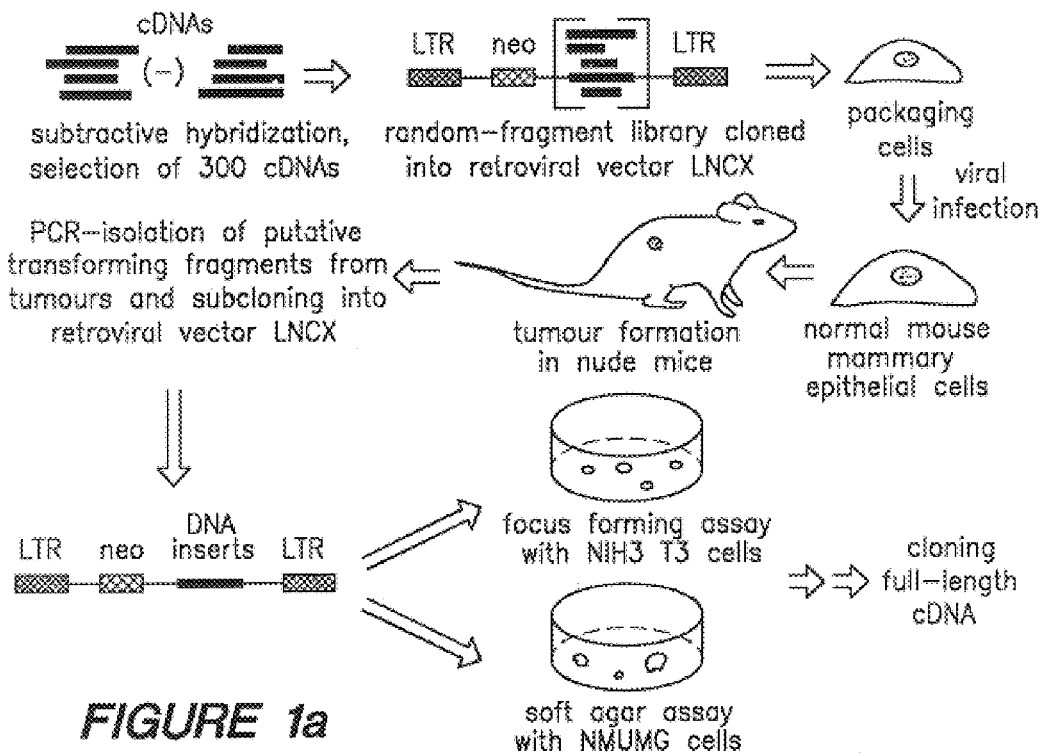
FIGURE 1a
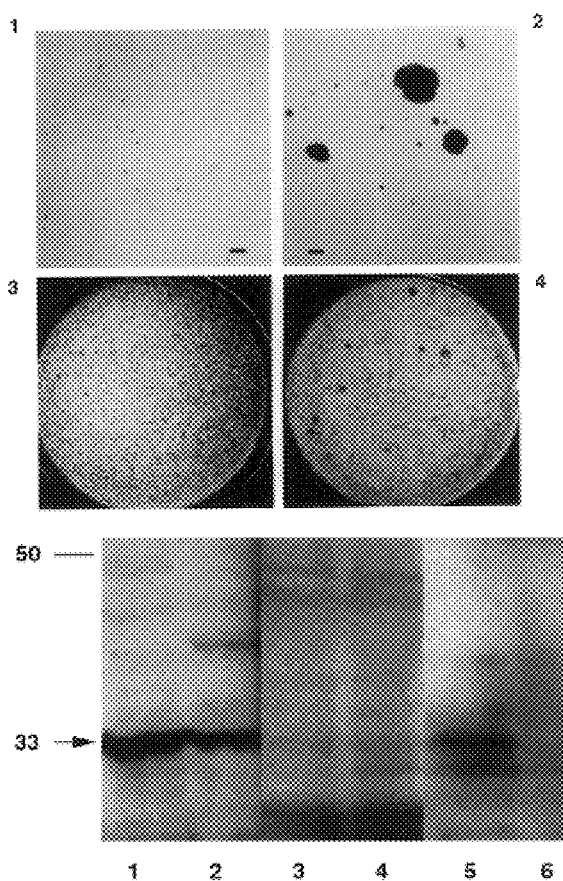
FIGURE 1b
FIGURE 1c

```
   1 CTG ACC CGA GGG TGG GGC CGC GCG TGG CCG TGG AAA CAG ATC CTG AAG GAG CTA GAC GAG

61 TGC TAC GAG CGC TTC AGT CGC GAG ACA GAC GGG GCG CAG AAG CGG CGG ATG CTG CAC TGT
   1                                                                 met leu his cys 121 GTG CAG CGC GCG CTG ATC CGC AGC CAG GAG CTG GGC GAC GAG AAG ATC CAG ATC GTG AGC
   5 val gln arg ala leu ile arg ser gln glu leu gly asp glu lys ile gln ile val ser 181 CAG ATG GTG GAG CTG GTG GAG AAC CGC ACG CGG CAG GTG GAC AGC CAC GTG GAG CTG TTC
  25 gln met val glu leu val glu asn arg thr arg gln val asp ser his val glu leu phe 241 GAG GCG CAG CAG GAG CTG GGC GAC ACA GTG GGC AAC AGC GGC AAG GTT GGC GCG GAC AGG
  45 glu ala gln gln glu leu gly asp thr val gly asn ser gly lys val gly ala asp arg 301 CCC AAT GGC GAT GCG GTA GCG CAG TCT GAC AAG CCC AAC AGC AAG CGC TCA CGG CGG CAG
  65 pro asn gly asp ala val ala gln ser asp lys pro asn ser lys arg ser arg arg gln 361 CGC AAC AAC GAG AAC CGT GAG AAC GCG TCC AGC AAC CAC GAC CAC GAC GAC GGC GCC TCG
  85 arg asn asn glu asn arg glu asn ala ser ser asn his asp his asp asp gly ala ser 421 GGC ACA CCC AAG GAG AAG AAG GCC AAG ACC TCC AAG AAG AAG AAG CGC TCC AAG GCC AAG
 105 gly thr pro lys glu lys lys ala lys thr ser lys lys lys lys arg ser lys ala lys 481 GCG GAG CGA GAG GCG TCC CCT GCC GAC CTC CCC ATC GAC CCC AAC GAA CCC ACG TAC TGT
 125 ala glu arg glu ala ser pro ala asp leu pro ile asp pro asn glu pro thr tyr cys 541 CTG TGC AAC CAG GTC TCC TAT GGG GAG ATG ATC GGC TGC GAC AAC GAC GAG TGC CCC ATC
 145 leu cys asn gln val ser tyr gly glu met ile gly cys asp asn asp glu cys pro ile 601 GAG TGG TTC CAC TTC TCG TGC GTG GGG CTC AAT CAT AAA CCC AAG GGC AAG TGG TAC TGT
 165 glu trp phe his phe ser cys val gly leu asn his lys pro lys gly lys trp tyr cys 661 CCC AAG TGC CGG GGG GAG AAC GAG AAG ACC ATG GAC AAA GCC CTG GAG AAA TCC AAA AAA
 185 pro lys cys arg gly glu asn glu lys thr met asp lys ala leu glu lys ser lys lys 721 GAG AGG GCT TAC AAC AGG TAG TTT GTG GAC AGG CGC CTG GTG TGA GGA GGA CAA AAT AAA
 205 glu arg ala tyr asn arg ***

781 CCG TGT ATT TAT TAC ATT GCT GCC TTT GTT GAG GTG CAA GGA GTG TAA AAT GTA TAT TTT
 841 TAA AGA ATG TTA GAA AAG GAA CCA TTC CTT TCA TAG GGA TGG CAG TGA TTC TGT TTG CCT
 901 TTT GTT TTC ATT GGT ACA CGT GTA ACA AGA AAG TGG TCT GTG GAT CAG CAT TTT AGA AAC
 961 TAC AAA TAT AGG TTT GAT TCA ACA CTT AAG TCT CAG ACT GAT TTC TTG CGG GAG GAG GGG
1021 GAC TAA ACT CAC CCT AAC ACA TTA AAT GTG GAA GGA AAA TAT TTC ATT AGC TTT TTT ATT
1081 TTA ATA CAA GTA ATA TTA TTA CTT TAT GAA CAA TTT TTT TTA ATT GGC CAT GTC GCC AAA
1141 AAT ACA GCC TAT AGT AAA TGT GTT TCT TGC TGC CAT GAT GTA TAT CCA TAT AAC AAT TCA
1201 GTA ACA AAG GTT TAA AGT TTG AAG ATT ATT TTT TAA AAA GGT AAA AGG TTA AAT TTT ACA
1261 TGA CAG ATA TTT TAT CTA TTG GCC TGT TCC CCA AAT GGC CAT TTT AAA ATG CTT GGG TAC
1321 ACT TCT CTT AAG TGG TCT AGT CAA GGA ACC TCA AGT CAT GCT TTT GCT ATC ACC AAT CAT
1381 AGT GTA CCC ATC TTT AAT TTA TAT CAG GTG TAT AAA TGT ACA TTT CCA AAT GAA CTT GCA
1441 CTG TAA TAT TAT AAT TGG AAG TGC AGT CAG CAG TAG CTG TCG GAG CTA ATG TCA CAA TTA
1501 TGT GCA AAG GTG TGC TTC CTG CTG TAT GTG AGC TGT AAA AAT GTT ACG TGA AGA AAT AAA
1561 TGA AAC TTG GCC AGT TTG TTC CTC TAG TAG TAT ATT TAA TTT TGA CAT AAG TAA CTT TTA
1621 AAA TTT GTC TTA AAA ATT TAT ACA CCA GCA ATT TAG ACA AAG CCT TAA GCA AAT TTT GTA
1681 TTA TTG TTC TCA CTT ATT ATT AAT AAT GAA GTA GAA GTT ACT TAA TTG CCA GCA AAT AAA
1741 TAC GTG TCA AAA AAG AAT CTG TAT TCA GAC CCC TGG GGT CAG GAA ATT ACT GCC CCA CTT
1801 GTC AAG TTC AGC CCA CCA TCT GTT TGA ACA TTA TAT GAA GTT TAA ATT CTA GTG TCC ATA
1861 AAT AAA GTT TCA GCG GCA CCC CAA AAA AAA AAA AAA AAA AAA
```

```
                                                      GAG TAA CCC GAT AAT
  16 ATG CCG TTG TGC ACG GCG ACG AGA ATT CCC AGA TAT AGC AGT AGC AGT GAT CCC GGG CCT
   1 met pro leu cys thr ala thr arg ile pro arg tyr ser ser ser ser asp pro gly pro
  76 GTG GCT CGG GGC CGG GGC TGC AGT TCG GAC CGC CTC CCG CGA CCC GCG GGG CCG GCT CGG
  21 val ala arg gly arg gly cys ser ser asp arg leu pro arg pro ala gly pro ala arg
 136 AGA CAG TTT CAG GCC GCA TCT TTG CTG ACC CGA GGG TGG GGC CGC GCG TGG CCG TGG AAA
  41 arg gln phe gln ala ala ser leu leu thr arg gly trp gly arg ala trp pro trp lys
 196 CAG ATC CTG AAG GAG CTA GAC GAG TGC TAC GAG CGC TTC AGT CGC GAG ACA GAC GGG GCG
  61 gln ile leu lys glu leu asp glu cys tyr glu arg phe ser arg glu thr asp gly ala
 256 CAG AAG CGG CGG ATG CTG CAC TGT GTG CAG CGC GCG CTG ATC CGC AGC CAG GAG CTG GGC
  81 gln lys arg arg met leu his cys val gln arg ala leu ile arg ser gln glu leu gly
 316 GAC GAG AAG ATC CAG ATC GTG AGC CAG ATG GTG GAG CTG GTG GAG AAC CGC ACG CGG CAG
 101 asp glu lys ile gln ile val ser gln met val glu leu val glu asn arg thr arg gln
 376 GTG GAC AGC CAC GTG GAG CTG TTC GAG GCG CAG CAG GAG CTG GGC GAC ACA GTG GGC AAC
 121 val asp ser his val glu leu phe glu ala gln gln glu leu gly asp thr val gly asn
                                                                          1
 436 AGC GGC AAG GTT GGC GCG GAC AGG CCC AAT GGC GAT GCG GTA GCG CAG TCT GAC AAG CCC
 141 ser gly lys val gly ala asp arg pro asn gly asp ala val ala gln ser asp lys pro
 496 AAC AGC AAG CGC TCA CGG CGG CAG CGC AAC AAC GAG AAC CGT GAG AAC GCG TCC AGC AAC
 161 asn ser lys arg ser arg arg gln arg asn asn glu asn arg glu asn ala ser ser asn
 556 CAC GAC CAC GAC GAC GGC GCC TCG GGC ACA CCC AAG GAG AAG AAG GCC AAG ACC TCC AAG
 181 his asp his asp asp gly ala ser gly thr pro lys glu lys lys ala lys thr ser lys
 616 AAG AAG AAG CGC TCC AAG GCC AAG GCG GAG CGA GAG GCG TCC CCT GCC GAC CTC CCC ATC
 201 lys lys lys arg ser lys ala lys ala glu arg glu ala ser pro ala asp leu pro ile
 676 GAC CCC AAC GAA CCC ACG TAC TGT CTG TGC AAC CAG GTC TCC TAT GGG GAG ATG ATC GGC
 221 asp pro asn glu pro thr tyr cys leu cys asn gln val ser tyr gly glu met ile gly
                                                    2
 736 TGC GAC AAC GAC GAG TGC CCC ATC GAG TGG TTC CAC TTC TCG TGC GTG GGG CTC AAT CAT
 241 cys asp asn asp glu cys pro ile glu trp phe his phe ser cys val gly leu asn his
 796 AAA CCC AAG GGC AAG TGG TAC TGT CCC AAG TGC CGG GGG GAG AAC GAG AAG ACC ATG GAC
 261 lys pro lys gly lys trp tyr cys pro lys cys arg gly glu asn glu lys thr met asp
                      3                             4
 856 AAA GCC CTG GAG AAA TCC AAA AAA GAG AGG GCT TAC AAC AGG TAG TTT GTG GAC AGG CGC
 281 lys ala leu glu lys ser lys lys glu arg ala tyr asn arg ***
 916 CTG GTG TGA GGA GGA CAA AAT AAA CCG TGT ATT TAT TAC ATT GCT GCC TTT GTT GAG GTG
 976 CAA GGA GTG TAA AAT GTA TAT TTT TAA AGA ATG TTA GAA AAG GAA CCA TTC CTT TCA TAG
1036 GGA TGG CAG TGA TTC TGT TTG CCT TTT GTT TTC ATT GGT ACA CGT GTA ACA AGA AAG TGG
1096 TCT GTG GAT CAG CAT TTT AGA AAC TAC AAA TAT AGG TTT GAT TCA ACA CTT AAG TCT CAG
1156 ACT GAT TTC TTG CGG GAG GAG GGG GAC TAA ACT CAC CCT AAC ACA TTA AAT GTG GAA GGA
1216 AAA TAT TTC ATT AGC TTT TTT ATT TTA ATA CAA GTA ATA TTA TTA CTT TAT GAA CAA TTT
1276 TTT TTA ATT GGC CAT GTC GCC AAA AAT ACA GCC TAT AGT AAA TGT GTT TCT TGC TGC CAT
1336 GAT GTA TAT CCA TAT AAC AAT TCA GTA ACA AAG GTT TAA AGT TTG AAG ATT ATT TTT TAA
1396 AAA GGT AAA AGG TTA AAT TTT ACA TGA CAG ATA TTT TAT CTA TTG GCC TGT TCC CCA AAT
1456 GGC CAT TTT AAA ATG CTT GGG TAC ACT TCT CTT AAG TGG TCT AGT CAA GGA ACC TCA AGT
1516 CAT GCT TTT GCT ATC ACC AAT CAT AGT GTA CCC ATC TTT AAT TTA TAT CAG GTG TAT AAA
1576 TGT ACA TTT CCA AAT GAA CTT GCA CTG TAA TAT TAT AAT TGG AAG TGC AGT CAG CAG TAG
1636 CTG TCG GAG CTA ATG TCA CAA TTA TGT GCA AAG GTG TGC TTC CTG CTG TAT GTG AGC TGT
1696 AAA AAT GTT ACG TGA AGA AAT AAA TGA AAC TTG GCC AGT TTG TTC CTC TAG TAG TAT ATT
1756 TAA TTT TGA CAT AAG TAA CTT TTA AAA TTT GTC TTA AAA ATT TAT ACA CCA GCA ATT TAG
1816 ACA AAG CCT TAA GCA AAT TTT GTA TTA TTG TTC TCA CTT ATT ATT AAT AAT GAA GTA GAA
1876 GTT ACT TAA TTG CCA GCA AAT AAA TAC GTG TCA AAA AAG AAT CTG TAT TCA GAC CCC TGG
1936 GGT CAG GAA ATT ACT GCC CCA CTT GTC AAG TTC AGC CCA CCA TCT GTT TGA ACA TTA TAT
1996 GAA GTT TAA ATT CTA GTG TCC ATA AAT AAA GTT TCA GCG GCA CCC CAA AAA AAA AAA AAA
2056 AAA AAA
```

Overexpression of p33$^{ING1}$ blocks cell growth

FIGURE 5a
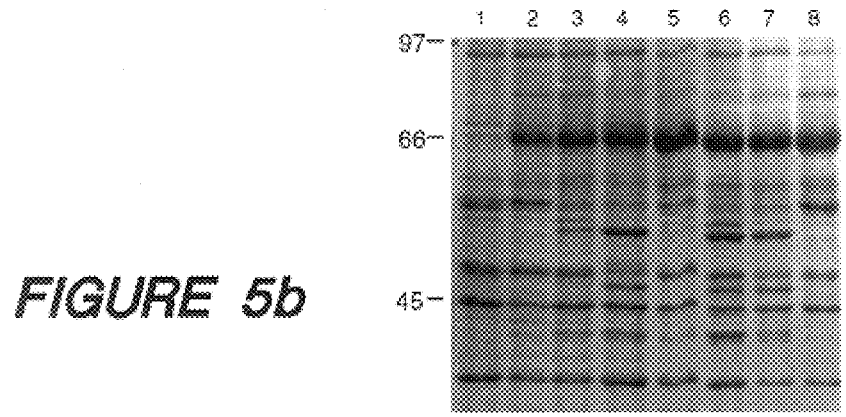
FIGURE 5b
Mutation of the *ING1* gene in neuroblastoma cell lines
FIGURE 6a
western blot
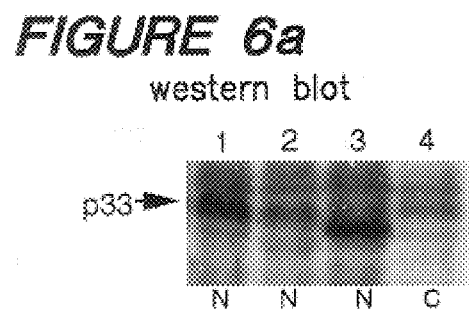
FIGURE 6b
restriction analysis
FIGURE 6c
PCR analysis
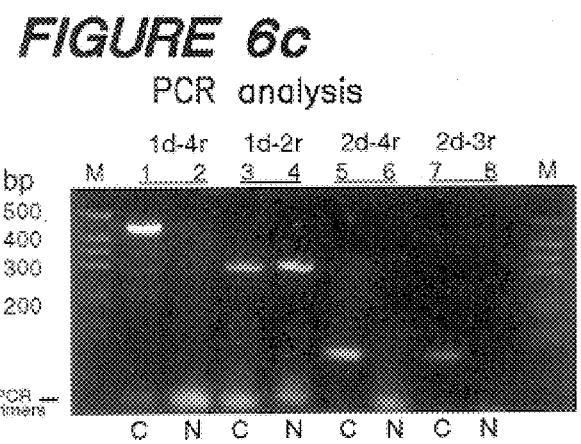

Expression of *ING1*/ p33$^{ING1}$ in
low & high passage primary HDFs mRNA levels by RT-PCR Protein levels by western blot Expression of p33$^{ING1}$ through the cell cycle
FIGURE 9a  cdk 2 →
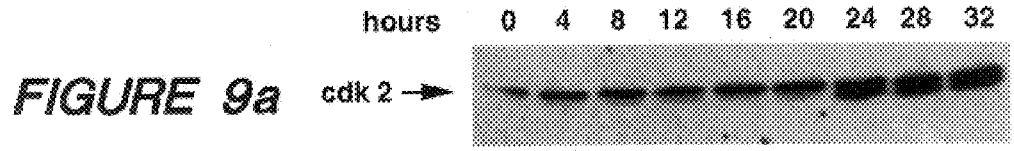
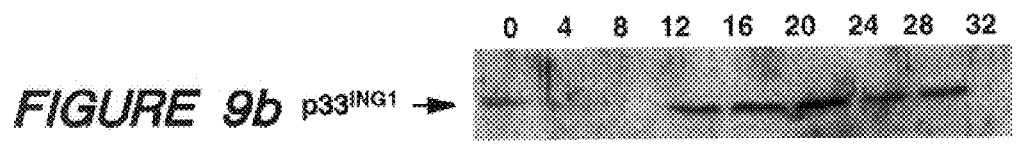
FIGURE 9b  p33$^{ING1}$ →
FIGURE 9c
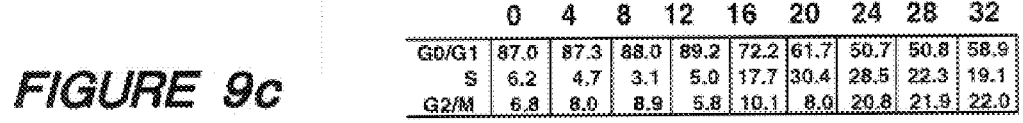
|  | 0 | 4 | 8 | 12 | 16 | 20 | 24 | 28 | 32 |
|---|---|---|---|---|---|---|---|---|---|
| G0/G1 | 87.0 | 87.3 | 88.0 | 89.2 | 72.2 | 61.7 | 50.7 | 50.8 | 58.9 |
| S | 6.2 | 4.7 | 3.1 | 5.0 | 17.7 | 30.4 | 28.5 | 22.3 | 19.1 |
| G2/M | 6.8 | 8.0 | 8.9 | 5.8 | 10.1 | 8.9 | 20.8 | 21.9 | 22.0 |

METHODS OF MODULATING APOPTOSIS

CROSS-REFERENCE TO RELATED APPLICATIONS

This application is a continuation of application Ser. No. 08/828,158, filed Mar. 27, 1997 and now abandoned. This application is a continuation-in-part of U.S. application Ser. No. 08/751,230 filed Nov. 15, 1996, which in turn is a continuation-in-part of U.S. application Ser. No. 08/569,721 filed Dec. 8, 1995 now U.S. Pat. No. 6,037,121, both of which are incorporated in their entirety by reference herein.

FIELD OF THE INVENTION

This invention relates to a method for modulating apoptosis in cells. The method of modulation involves using a protein, ING1, and related proteins and peptides, nucleic acids encoding this and related proteins and peptides, and nucleic acids complementary to nucleic acids encoding $p33^{ING1}$.

This invention also relates to a method for determining the apoptotic characteristic of cells using oligonucleotides from the ING1 gene, $p33^{ING1}$ peptides and antibodies directed against $p33^{ING1}$ peptides.

REFERENCES

The following references are cited in the application as numbers in brackets ([ ])at the relevant portion of the application.

1. Levine, A. J., "The Tumor Suppressor Genes", *Annu. Rev. Biochem.* 62:623–651 (1993).
2. Hunter, T. et al., "Cyclins and Cancer II: Cyclin D and CDK Inhibitors Come of Age", *J. Cell* 79:573–582 (1994).
3. Gudkov, A. V. et al., "Isolation of genetic suppressor elements, inducing resistance to topoisomerase II-interactive cytotoxic drugs, from human topoisomerase II cDNA", *Natl. Acad. Sc. USA* 90:3231–3235 (1993).
4. Straus, D. et al., "Genomic subtraction for cloning DNA corresponding to deletion mutations", *Proc. Natl. Acad. Sc. USA* 87:1889–1893 (1990).
5. Lisitsyn, N. et al., "Cloning the Differences Between Two Complex Genomes", *Science* 259:946–951 (1993).
6. Yaswen, P. et al., "Down-regulation of a calmodulin-related gene during transformation of human mammary epithelial cells", *Proc. Natl. Acad. Sc. USA* 87:7360–7364 (1990).
7. Miller, A. D. et al., "Improved Retroviral Vectors for Gene Transfer and Expression", *Biotechniques* 7:980–986 (1989).
8. Serrano, M. et al., "A new regulatory motif in cell-cycle control causing specific inhibition of cyclin D/CDK4", *Nature* 366:704–707 (1993).
9. Defeo-Jones, D., "Cloning of cDNAs for cellular proteins that bind to the retinoblastoma gene product", *Nature* 352:251–254 (1991).
10. Aharon, T. et al., "Selective Destabilization of Short-Lived mRNAs with the Granulocyte-Macrophage Colony-Stimulating Factor AU-Rich 3' Noncoding Region is Mediated by a Cotranslational Mechanism", *Mol. Cell. Biol.* 13:1971–1980 (1993).
11. Guan, K. et al., "Growth suppression by p18, a $p16^{INK4/MTS1}$ and $p14^{INK4B/MTS2}$-related CDK6 inhibitor, correlates with wild-type pRb function", *Genes & Dev.* 8:2939–2952 (1994).
12. Harper, J. W. et al., "The p21 Cdk-Interacting Protein Cip1 is a Potent Inhibitor of G1 Cyclin-Dependent Kinases", *Cell* 75:805–816 (1993).
13. El-Deiry, W. S. et al., "WAF1, a Potential Mediator of p53 Tumor Suppression", *Cell* 75:817–825 (1993).
14. Kamb, A. et al., "A Cell Cycle Regulator Potentially Involved in Genesis of Many Tumor Types", *Science* 264:436–440 (1994).
15. Nobori, T. et al., "Deletions of the cyclin-dependent kinase-4 inhibitor gene in multiple human cancers", *Nature* 368:753–756 (1994).
16. Riabowol, K. et al., "The cdc2 Kinase Is a Nuclear Protein That Is Essential for Mitosis in Mammalian Cells", *Cell* 57:393–401 (1989).
17. Sambrook, J. et al., "Molecular Cloning" (2nd.Ed.), *A Laboratory Manual, Cold Spring Harbor Laboratory Press* (1989).
18. Harlow, E. et al., "Antibodies", *A Laboratory Manual, Cold Spring Harbor Laboratory* (1988).
19. Yang, Y. et al., "An approach for treating the hepatobiliary disease of cystic fibrosis by somatic gene transfer" *Proc. Nat'l. Acad. Sci. USA* 90:4601–4605 (1993).
20. Atadja, P. et al., "Increased activity of p53 in senescing fibroblasts" *Proc. Nat'l. Acad. Sci. USA* 92:8348–8352 (1995).
21. Demetrick, D. J. "Fluorescence in situ hybridization and human cell cycle genes" *In the Cell Cycle—Materials and Methods* M. Pagano (ed.) Springer Verlag Press, 29–45 (1995).
22. Motomura et al., "Loss of alleles at loci on chromosome 13 in human primary gastric cancers" *Genomics* 2, 180–184 (1988).
23. Mitelman et al., "Report of the committee on chromosome changes in neoplasia" *Cytogenet Cell Genet* 55:358–386 (1990).
24. Maestro et al., "Chromosome 13q deletion mapping in head and neck squamous cell carcinomas: identification of two distinct regions of preferential loss" *Cancer Research* 56:1146–1150 (1996).
25. Thompson, M. E. et al., "Decreased expression of BRCA-1 accelerates growth and is often present during sporadic breast cancer progression" *Nature Genetics* 9:444–450 (1995).
26. Pear, W. S. et al., "Production of high titer helper-free retroviruses by transient transfection" *Proc. Natl. Acad. Sci.* 90:8392–8396 (1993).
27. Wong, H. et al., "Monitoring mRNA expression by polymerase chain reaction: the "primer-dropping" method" *Anal. Biochem.* 223:251–258 (1994).
28. Schneider E. L and Fowlkes, B. J., "Measurement of a DNA content and cell volume in senescent human fibroblasts utilizing flow miltiparameter single cell analysis" *Exp. Cell. Res.* 98:298–302 (1976).
29. Tsai, L. H. et al., "The cdk2 kinase is required for the G1- to —S transition in mammalian cells" *Oncogene* 8:1593–1602 (1993).
30. Bond, et al., "Escape from senescence in human diploid fibroblasts induced directly by mutant p53" *Oncogene* 9:1885–1889 (1994).
31. Graessmann and Graessmann, "Microinjection of tissue culture cells", *Methods in Enzymology* 101:482–492 (1983).
32. Smith et al., "antibodies to CD3/T-cell receptor complex induce death by apoptosis in immature T cells in thymic cultures", *Nature* 337:181–184 (1989).

33. Meikrantz and Schlegel "Apoptosis and the cell cycle" *J. Cell. Biochem* 58:160–174 (1995).

34. Lee and Bernstein "Apoptosis, cancer and the p53 tumor suppressor gene" *Cancer Met Rev.* 14:149–161 (1995).

35. Galli & Fratelli, "activation of apoptosis by serum deprivation in a teratocarcinoma cell line: inhibition by Lacetycarnitine", *Exp. Cell Res.* 204:54–60 (1993).

36. Gossen and Bujard, "Tight control of gene expression in mammalian cells by tetracycline-responsive promoters", *Proc. of Natl Acad. Sci.* 89(12):5547–5551 (1992).

37. Garkavtsev et al. "Suppression of the novel growth inhibitor ING1 promotes neoplastic transformation" *Nature Gen.* 14:415–420 (1996).

The disclosure of the above publications, patents and patent applications are herein incorporated by reference in their entirety to the same extent as if the language of each individual publication, patent and patent application were specifically and individually included herein.

BACKGROUND OF THE INVENTION

Apoptosis is a form of programmed cell death which occurs through the activation of cell-intrinsic suicide machinery. The biochemical machinery responsible for apoptosis is expressed in most, if not all, cells. Apoptosis is primarily a physiologic process necessary to remove individual cells that are no longer needed or that function abnormally. Apoptosis is a regulated event dependent upon active metabolism and protein synthesis by the dying cell.

Apoptosis plays a major role during development and homeostasis. Apoptosis can be triggered in a variety of cell types by the deprivation of growth factors, which appear to repress an active suicide response. Apoptosis is particularly important for the physiology of the immune system. Apoptosis is the mode of death of centroblasts with low affinity for antigen within germinal centers, cells killed by specific cytotoxic T lymphocytes or natural killer cells, as well as thymocytes bearing high-affinity T-cell receptors for self antigens that are clonally deleted during thymus development (negative selection).

The morphological and biochemical characteristics of cells dying by apoptosis differ markedly from those of cells dying by necrosis. During apoptosis, cells decrease in size and round up. The nuclear chromatin undergoes condensation and fragmentation. Cell death is preceded by DNA fragmentation. The DNA of apoptotic cells is nonrandomly degraded by endogenous calcium and magnesium-dependent endonuclease(s) inhibited by zinc ions. This enzyme(s) gives fragments of approx. 200 base pairs (bp) or multiples of 200 bp by cutting the linker DNA running between nucleosomes. Thus DNA appears to be one of the most important targets of the process that leads to cell suicide. The apoptotic cell then breaks apart into many plasma membrane-bound vesicles called "apoptotic bodies," which contain fragments of condensed chromatin and morphologically intact organelles such as mitochondria. Apoptotic cells and bodies are rapidly phagocytosed, thereby protecting surrounding tissues from injury. The rapid and efficient clearance of apoptotic cells makes apoptosis extremely difficult to detect in tissue sections.

In contrast, necrosis is associated with rapid metabolic collapse that leads to cell swelling, early loss of plasma membrane integrity, and ultimate cell rupture. Cytosolic contents leach from the necrotic cell causing injury and inflammation to surrounding tissue.

Recent studies show that multiple cytotoxic stimuli well known to cause necrosis can lead to apoptosis instead when cells are exposed to the same noxious agents at lower concentrations. This insight has led to an interest in the role of apoptosis in the pathogenesis of renal diseases that result primarily from injury to renal tubular epithelial cells. These diseases include acute and chronic renal failure from exposure of the kidney to ischemia or to cytotoxic agents. There is also an interest in the role of apoptosis in Alzheimers and other neurological diseases.

Several genes associated with apoptosis have been identified. Examples include the p53 gene, which is involved in osteosarcoma and adrenocortical, breast and brain cancers;

The gene cloned and sequenced as described herein, ING1 (formerly called $p33^{IG1}$), represents a new gene which is expressed in normal mammary epithelial cells, but expressed only at lower levels in several cancerous mammary epithelial cell lines and is not expressed in many primary brain tumors.

SUMMARY OF THE INVENTION

The present invention is directed to a method to potentiate apoptosis in a eukaryotic cell, which method comprises selecting said eukaryotic cell; and increasing the $p33^{ING1}$ biological activity in said eukaryotic cell. It is contemplated that the $p33^{ING1}$ biological activity in said eukaryotic cell may be increased by introducing into said eukaryotic cell an effective amount of a peptide comprising $p33^{ING1}$ biological activity or by introducing into said eukaryotic cell an effective amount of an oligonucleotide which codes for a peptide comprising $p33^{ING1}$ biological activity under conditions such that a peptide comprising $p33^{ING1}$ biological activity is expressed by the cell.

Another aspect of the invention provides a method to inhibit apoptosis of a eukaryotic cell, which method comprises selecting said eukaryotic cell; and reducing the effective quantity of $p33^{ING1}$ biological activity in said eukaryotic cell. It is contemplated that the effective quantity of $p33^{ING1}$ biological activity may be reduced by administering to the cell a single-stranded oligonucleotide of at least 20 nucleotides which comprises a sequence substantially identical to the complement of the cDNA sequence of FIG. 3 or by administering to the cell a double-stranded oligonucleotide which comprises a sequence substantially identical to the cDNA sequence of FIG. 3 under conditions such that a nucleic acid of at least 20 nucleotides having a sequence which is substantially identical to the complement of the cDNA sequence of FIG. 3 is expressed. It is also contemplated that the effective quantity of $p33^{ING1}$ biological activity may be reduced by inactivating the ING1 gene in the cell.

Another aspect of the invention provides a method for determining the apoptotic characteristic of a eukaryotic cell which method comprises selecting said cell; and determining the level of expression of native $p33^{ING1}$ in said cell and comparing it to the level of expression of native $p33^{ING1}$ in a non-apoptotic cell wherein an increased level of $p33^{ING1}$ expression in the cell denotes a cell having the potential to be apoptotic. It is contemplated that the level of expression may be determined by exposing the cell to detectably labelled anti-ING1 antibodies or by exposing the cell to a detectably labelled single-stranded oligonucleotide of at least 100 nucleotides which comprises a sequence substantially identical to the complement of the cDNA sequence of FIG. 3 under conditions such that the oligonucleotide will bind to any ING1 mRNA present in the cell to determine the level of expression of mRNA ING1 in the cells. It is also contemplated that the level of expression may be determined by exposing the cell to two single-stranded oligonucleotides of from 15 to 25 nucleotides in length, wherein the first oligonucleotide binds to one region of the ING1 mRNA and the second oligonucleotide binds to a sequence complementary to another region of the ING1 cDNA under conditions wherein polymerase chain reaction can occur and any ING1 mRNA in the cell will be amplified and labelled.

A still further aspect of the invention provides an assay for determining the level of $p33^{ING1}$ activity in a eukaryotic cell, which assay comprises selecting the eukaryotic cell; determining the $p33^{ING1}$ biological activity in the cell; and correlating the biological activity against a curve of the $p33^{ING1}$ biological activity in certain cell types.

A still further aspect of the invention is an isolated eukaryotic cell substantially free of $p33^{ING1}$ biological activity.

BRIEF DESCRIPTION OF THE DRAWINGS

FIGS. 1A to 1C illustrate the strategy and biological assays used for cloning ING1.

FIG. 2 sets forth the partial cDNA sequence of ING1 (SEQ ID NO: 1) and the predicted amino acid sequence (SEQ ID NO: 2) of $p33^{ING1}$.

FIG. 3 sets forth the complete cDNA sequence of ING1 (SEQ ID NO: 9) and the predicted amino acid sequence (SEQ ID NO: 10) of $p33^{ING1}$.

FIGS. 5A–5B illustrate the changes in $p33^{ING1}$ protein levels in breast cancer cell lines. FIG. 5A is a Western blot. FIG. 5B is a picture of the coomassie-blue stained gel of FIG. 5A.

FIG. 6A illustrates Western blotting of neuroblastoma cell lines with anti-$p33^{ING1}$ antibody. FIG. 6B illustrates a Southern blot of neuroblastoma cell line compared to a normal diploid cell strain for ING1 DNA. FIG. 6C illustrates the RT-PCR reaction on a neuroblastoma cell line compared to a control diploid fibroblast.

FIGS. 9A–9C illustrate the level of $p33^{ING1}$ protein through the cell cycle. FIG. 9A has anti-cdk2 antibody as a positive control. FIG. 9B shows the results with anti-p33 antibodies. FIG. 9C shows cell cycle profile at each point as determined by FACS.

FIG. 11A shows a Western Blot of protein homogenates probed with a polyclonal antibody specific for ING1. FIG. 11B shows a trypan blue dye exclusion assay of serum starved P19 cells infected with retroviral constructs expressing antisense ING1 (aS), sense ING1 (s), bcl-2 sense (S-bcl-2), bcl-2 antisense (aS-bcl-2) and vector only (V) constructs.

FIG. 13A illustrates cell viability of NIH-3T3 tet-myc cells containing antisense (αS), sense (S) ING1 or vector only (v) constructs. FIG. 13B illustrates the amount of DNA laddering in tet-myc cells expressing ING1 sense (S), antisense (αS), vector (v), bcl-2 and control (c) without vector. FIG. 13C illustrates the effect on cell viability of microinjection of GST-ING1 protein.

DETAILED DESCRIPTION OF THE INVENTION

Figure 4A:
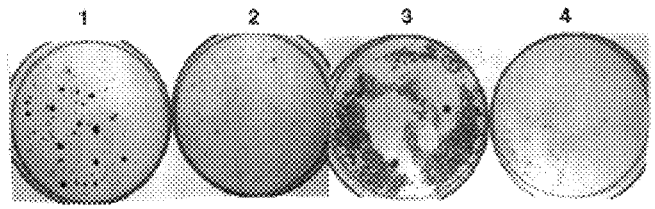
FIGS. 4A to 4C illustrate the effects of $p33^{ING1}$ overexpression.

The invention described herein relates to the discovery of a method for the modulation of apoptosis in eukaryotic cells. The invention also relates to a method for detecting cells having and/or lacking the potential to undergo apoptosis.

Using a strategy based upon subtractive hybridization of normal and cancerous mammary epithelial cell mRNAs and the selection of genetic suppressor elements [3], a novel gene was isolated encoding a 33 kDa protein that is a potent inhibitor of cell growth. Acute expression of transfected constructs encoding $p33^{ING1}$ induced apoptosis in cells. Inhibition of translation of the mRNA for this gene prevented apoptosis in cells.

A. Definitions

As used herein the following terms have the following meanings:

"Antibody" means a molecule that binds to a known antigen. An "anti-$p33^{ING1}$ antibody" means an antibody molecule that binds to one or more epitopes of the $p33^{ING1}$ protein.

"Antisense" and "Antisense nucleotides" means DNA or RNA constructs which block the expression of the naturally-occurring gene product. For example, in the present invention, use of a DNA construct that produces ING1 antisense RNA blocks the expression of $p33^{ING1}$ by destroying or inactivating ING1 mRNA.

"Apoptosis" means a form of programmed cell death.

The "apoptotic characteristic" of a cell is the ability of a cell to undergo apoptosis when exposed an apoptotic triggering event. Such events include, for example, exposure to certain toxins and/or expression of a tumorigenic gene or activation of cell surface proteins.

"Biological sample" means a sample of eukaryotic cells. These cells may be part of a tissue or organ sample obtained, for example, by biopsy, or they may be individual cells, for example, blood cells or cells grown in tissue culture.

"Cancerous cell" means a cell in or from a neoplasm. Preferably the cancerous cells is breast cancer, brain cancer, gastric cancer, hematologic neoplasms and head and neck squamous cell carcinomas.

"Breast cancer" means any of various malignant neoplasms of the breast or mammary tissue.

"Brain cancer" means any of various malignant neoplasms of the brain, neuroglial cells or meninges.

"Cell cycle" means the cyclic biochemical and structural events occurring during growth of cells. The cycle is divided into periods called quiescence ($G_0$), Gap$_1$ ($G_1$), DNA synthesis (S), Gap$_2$ ($G_2$), and mitosis (M).

"Cell division" means mitosis, i.e., the usual process of cell reproduction.

"Code" or "encode", when used with reference to a nucleotide's relation to a protein, mean the system whereby particular combinations of adjacent nucleotides control the insertion of particular amino acids in equivalent places in a protein molecule.

"Expression" means the production of a protein or polynucleotide in the cell.

A "eukaryotic cell" is a cell having a membrane-bound nucleus containing DNA in the form of chromosomes, either in a tissue or organ or in tissue culture. More preferably, it is a mammalian cell.

"Growth" means progression through the cell cycle with the result that two daughter cells are formed from each mother cell. "Actively growing" means that state wherein cells exhibit growth and cell division.

"Hyperplasticity" means an increase in cell number, excluding tumor formation.

"Immunohistochemistry" means a method to localize a specific protein within a cell using cell sections or thin sections of a specific tissue and an antibody directed against the target protein. It is contemplated that the antibody may be directly labelled, radioactively, biotinylated or labelled with a fluorochrome. It is also contemplated that the antibody may be indirectly labelled.

"Inactivating" a gene means rendering the gene incapable of producing an active protein normally encoded by that gene. Methods of inactivating a gene include, for example, deleting the gene in the cell or introducing a deletion or mutation into the gene such that the gene no longer expresses an active protein. Preferably cells having such inactivated genes are substantially free of the active protein.

"In situ hybridization" means a method to identify and localize certain specific transcripts of specific genes in cells and tissue sections. The cells are fixed to a solid support and hybridized to a labelled nucleic acid probe complementary to the sequence to be identified. The probe may be directly labelled or indirectly labelled.

"Label" means to incorporate into a compound a substance that is readily detected. Such substances include radioactive substances and fluorescent dyes, for example.

"Mammalian cell" means a cell in or from a mammal, either in a tissue or organ or in tissue culture.

"Neoplasia" means the process resulting in the formation and growth of an abnormal tissue that grows by cellular proliferation more rapidly than normal, and continues to grow after the stimuli that initiated the new growth cease.

"Neoplastic" describes the abnormal tissue that grows by cellular proliferation more rapidly than normal, and continues to grow after the stimuli that initiated the new growth cease.

"Normal cell" means a non-cancerous cell.

"Proliferation" means growth and reproduction, i.e., division of cells. "Actively proliferating" means cells that are actively growing and reproducing.

"Native" means the nucleic acid of a non-mutated gene or peptide sequence encoded by such a gene as found in a phenotypically normal cell.

"Substantially identical" means that the polynucleotide or nucleic acid of interest is able to hybridize to the complement of the known sequence under stringent conditions. Such stringent conditions preferably require at least 85% homology, more preferably the conditions require at least 90% homology and most preferably the conditions require at least 95% homology. When used in relation to peptides and proteins, "substantially identical" means that the amino acid sequence of the peptides share at least 85% homology, more preferably at least 90% homology and most preferably at least 95% homology.

"Senescent cells" means cells that are no longer actively dividing and reproducing. Such cells are typically characterized by an inability to respond to growth factors and by altered morphology including increased size and decreased saturation density in tissue culture.

B. Synthesis and Methodology

A novel positive selection procedure that combines subtractive hybridization with an in vivo selection assay was used to identify putative growth-suppressor elements. An overview of the strategy used is shown in FIG. 1A.

Following a modified subtractive hybridization protocol [4,5], total cDNA from a normal mammary epithelial cell line [6] was hybridized independently with cDNAs from the breast cancer cell lines MCF-7, BT-483, BT-474, Hs-578T, ZR-75, MD-MB-468, MD-MB-435 and BT-20 which were obtained from the American Type Culture Collection. Subtracted cDNA, theoretically containing sequences more highly expressed in the phenotypically normal epithelial cells, was then used as a probe to screen a normal human fibroblast cDNA library.

Following screening, 300 cDNA clones were isolated, and their inserts were digested into fragments of 200–800 base pairs. The fragments were then recloned into the retroviral plasmid vector pLNCX [7]. After passage through the packaging line BOSC 23 [3], retroviruses containing the isolated fragments were used to infect normal mouse mammary epithelial cells (NMuMG). The infected cells were subsequently injected into nude mice.

Within 45 days, several mice developed tumors from which the cloned inserts were recovered by amplification using primers specific for pLNCX in polymerase chain reactions (PCR). Two different sequences were isolated from tumors, one of which was subsequently shown to be expressed in the antisense orientation.

The antisense sequence isolated, when introduced into normal fibroblast cells, consistently showed the biological effects of increased cell proliferation in soft agar and in focus forming assays (FIG. 1B and Table 1). This 182 bp fragment represented nucleotides 781 to 963 of the cDNA shown in FIG. 2 and nucleotides 942 to 1124 of FIG. 3. This cDNA encodes a 33 kDa protein called p33$^{ING1}$ for INhibitor of Growth. This was formerly designated p33$^{IG1}$ (see U.S. Ser. No. 08/569,721 which is incorporated herein by reference in its entirety).

After plating NMuMG cells infected with either control virus or with virus containing an insert of the antisense orientation of ING1 in soft agar, cells receiving the insert formed, on average, at least 50 times the number of colonies as cells infected with virus alone. Similar results were obtained following transfection of the retroviral construct into NIH3T3 cells, where pLNCX containing the insert of the antisense orientation of ING1 resulted in the formation of 2.3 times the number of generally larger foci than vector alone.

These results corroborated the observations made in the nude mouse assay that the ING1 sequence corresponds to a gene whose product plays a significant role in regulating cell growth.

In order to isolate the gene corresponding to the fragment showing biological effects, normal human fibroblast and HeLa cell libraries were screened with the fragment, resulting in the isolation of 11 positive clones. Two clones contained cDNA whose sequence is shown in FIG. 2. The complete cDNA sequence (FIG. 3) was obtained using rapid amplification of cDNA ends (RACE) by methods known in the art.

Comparison of the sequence of p33$^{ING1}$ shown in FIG. 3 to the available protein and nucleotide data bases showed no significant homology to any sequence encoding a known protein and very limited similarity to retinoblastoma binding protein 2 (RbBP2) [9] and to several zinc finger transcription factors. Regions of the p33$^{ING1}$ protein that show homology to retinoblastoma binding protein 2 were identified using the Blast program available from the National Centre for Biological Information (address: www.ncbi.nim.nih.gov).

Use of a polyclonal antibody raised against a glutathione-S-transferase (GST) fusion with p33$^{ING1}$ revealed a protein of 33 kDa by Western blot analysis of human and mouse cell extracts (FIG. 1C).

To determine whether the level of p33$^{ING1}$ was decreased in cells infected with viral constructs containing the antisense orientation, lysates were prepared from control NMuMG cells and from NMuMG cells infected with antisense ING1 that had grown and formed colonies in semisolid medium. Results of Western blot analysis showed that chronic expression of antisense construct reduced the expression of the endogenous p33$^{ING1}$ protein by approximately 90% in the cells (FIG. 1C, lane 6) compared to control parental cells (FIG. 1C, lane 5).

The ING1 cDNA contains several AU-rich elements (AREs) in the 3' untranslated region of the clone (FIG. 2) which are believed to be involved in the destabilization of specific mRNAs [10].

Since the ING1 gene was originally isolated by subtractive hybridization between normal and transformed epithelial cDNAs, the levels of ING1 mRNA expression in different normal, breast cancer, and brain cancer cell lines were examined. Results from Northern blot analysis show that ING1 is expressed at considerably lower levels (approximately 2–8 fold as estimated by scanning densitometry) in BT-20, ZR-75, MDA-MB-435 and T-47D breast cancer cells compared to MDA-MB-468 and SK-BR-3 breast cancer cells and to normal Hs68 fibroblasts. Results from reverse transcription polymerase chain reaction (RT-PCR) showed that ING1 is not expressed or is expressed at very low levels in glioblastomas, astrocytomas and meningiomas.

Isolation of a DNA fragment that was capable of inducing tumors, foci and growth in soft agar when expressed in the antisense orientation, suggested that the cellular role of p33$^{ING1}$ is to negatively regulate growth. To test this idea, part of the ING1 cDNA was cloned into the mammalian expression vector pBK in the sense orientation (pING1-S). This construct and the plasmid vector, both of which contain neomycin resistance genes and a cytomegalovirus (CMV) promoter, were transfected into human breast cancer (Hs578T) and normal fibroblast (Hs68) cells. Following growth of the cells in antibiotic for 3 weeks, a large number of stable transformants were recovered from cells transfected with vector (1+3), whereas very few colonies were visible in plates of cells transfected with the sense orientation of ING1 cDNA (2+4)(FIG. 4A).

To corroborate the results of these chronic assays, the effect of microinjecting these constructs, together with non-specific antibodies into fibroblasts was examined. Arrows in panels 1 and 3 of FIG. 4B identify cells injected with sense (S) and antisense (αS) constructs, respectively, which were visualized by staining for the presence of coinjected non-specific antibodies using indirect immunofluorescence.

Figure 4B:
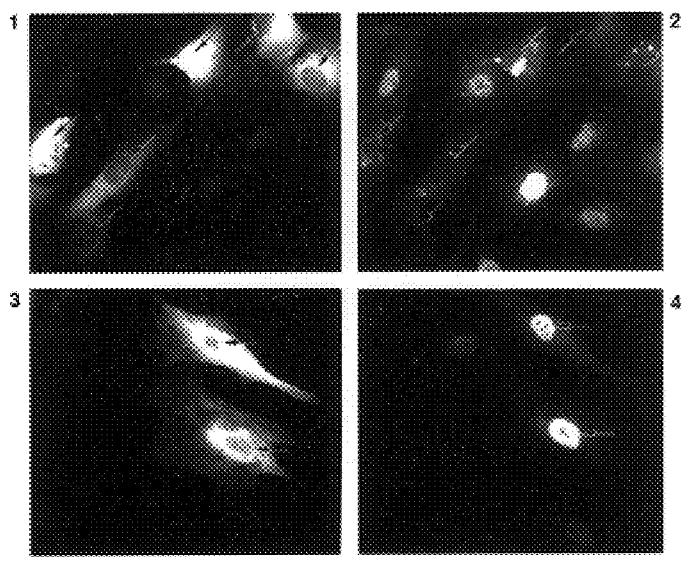

Arrows in panels 2 and 4 of FIG. 4B show that cells injected with pING1-S failed to incorporate bromodeoxyuridine (BrdU) (panel 2) over a 36 hour time course after injection. In contrast, those injected with pING1-αS entered S phase (panel 4) as estimated by staining with anti-BrdU antibodies.

Figure 4C:
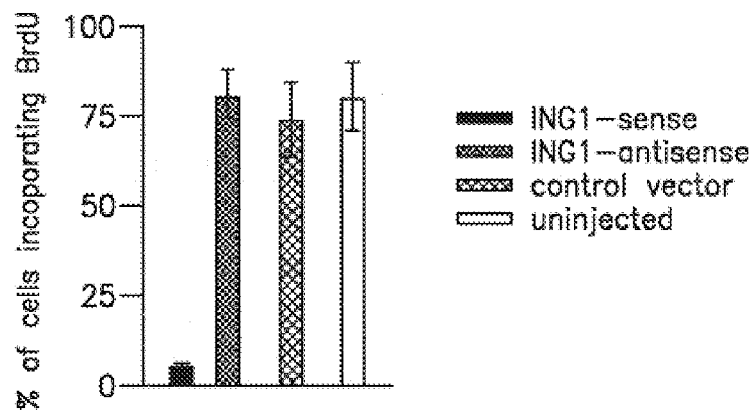

FIG. 4C shows the combined results of 5 separate experiments, which indicated that injection of the pBK vector or of pING1-αS constructs had no appreciable effect upon the ability of injected cells to incorporate BrdU, whereas injection of pING1-S blocked the ability of cells to enter into and proceed through S phase.

Similar results were obtained in larger populations of cells that were electroporated with vector, sense and antisense construct DNAs together with a construct encoding the CD20 surface marker. Such co-transfections allowed the analysis of DNA content in cells that had taken up DNA by staining for CD20 and subsequent analysis by fluorescence activated cell sorting (FACS). As shown in Table 2, the CD20-expressing population co-transfected with pING1-S had, on average, 63.1% of cells in G0/G1 whereas those co-transfected with vector had 33.6% of cells in G0/G1 when cells were fixed and stained 48 hours after electroporation.

These results, using several independent methods, indicate that the overexpression of p33$^{ING1}$ inhibits cell growth and DNA synthesis in both transient and chronic assays, most likely by arresting cells in the G1 phase of the cell cycle.

Figure 8A:
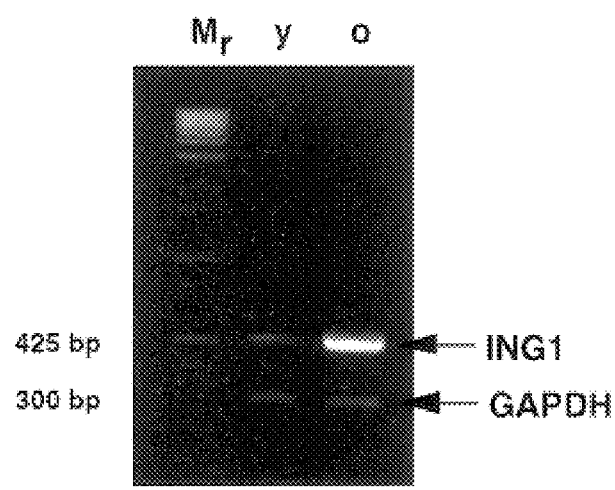
FIGS. 8A and 8B illustrate the expression of ING1 mRNA and $p33^{ING1}$ in proliferation competent (y) and in senescent human fibroblasts (o).
Figure 8B:
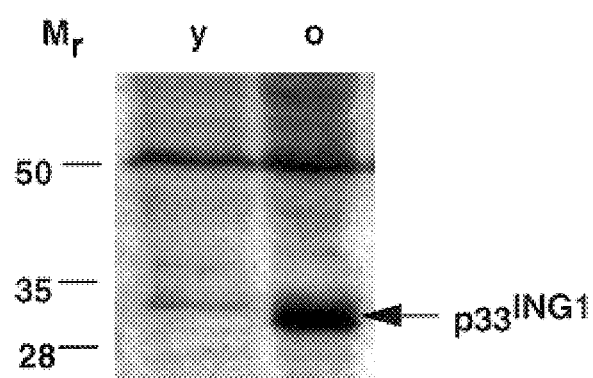

Since the activity of the tumor suppressor genes increases in senescent cells [20], p33$^{ING1}$ activity in low and high passage cells was checked. As shown in FIGS. 8A and 8B, ING1 expression (and the level of the p33$^{ING1}$ protein) increased several-fold when cells approached the end of their in vitro replicative lifespan.

These data demonstrate that p33$^{ING1}$ is a novel inhibitor of cell growth and a candidate tumor suppressor. Additional experiments also indicate that p33$^{ING1}$ is localized in the nucleus of cells, which is consistent with p33$^{ING1}$'s functioning as a tumor suppressor. Further data showed that ING1 gene is localized to the 13q33-34 chromosome region. A number of human cancers have been mapped to this region including primary gastric cancer; hematologic neoplasms; head and neck squamous cell carcinomas. Alternatively, p33$^{ING1}$ might play a role in the regulation of cyclin-dependent kinases (CDKs), as reported recently for the family of CDK inhibitors including p18[11], p21[12,13] and the candidate tumor suppressor p16$^{MTS1}$[8] to which a portion of the p33$^{ING1}$ sequence shows some homology, and which has been reported to be the MTS1 multiple tumor suppressor locus of human chromosome 9p21 that is inactivated in many types of human tumors [14,15].

Figure 12A:
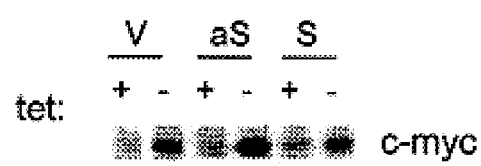
FIG. 12A illustrates a Western blot of human c-myc and ING1 expression in NIH 3T3 tet-myc cells retrovirally infected with constructs containing vector (v), antisense (αS) and sense (S) ING1 constructs grown in the presence (+) or absence (−) or tetracycline.
Figures 12B, 12C, 12D:
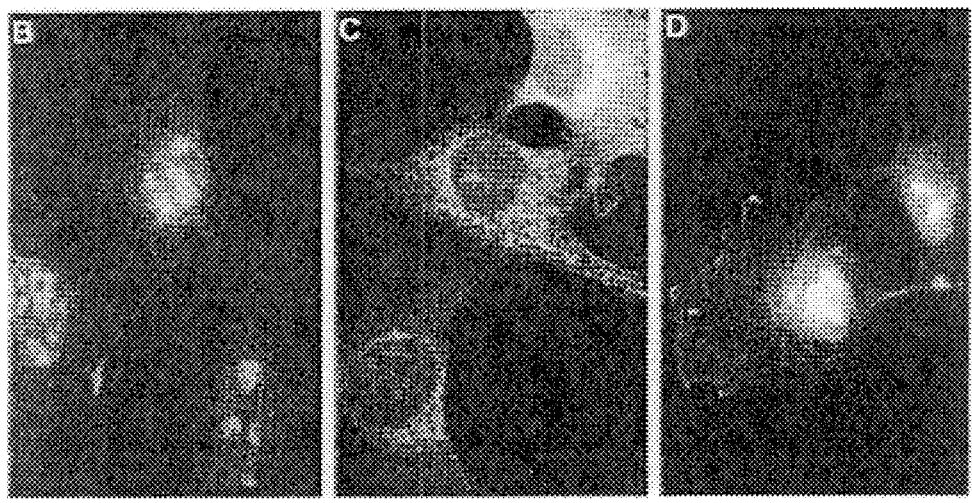
FIGS. 12B–12D are pictures of cells having vector only (FIG. 12B), ING1 antisense construct (FIG. 12C) or ING1 sense construct (FIG. 12D) fixed and stained with labelled anti-ING1 antibody.

Indications that the ING1 gene may be involved in the modulation of apoptosis first came from the conspicuous presence of p33$^{ING1}$ in regressing tail and its absence from growing hindlimbs of metamorphosing Xenopus tadpoles. Accordingly, P19 cells were infected with sense (S), antisense (αS) constructs and cell viability was examined under serum starvation. As shown in FIG. 12B, the antisense construct conferred a moderate level of protection against death (70% viability). Conversely, P19 cells expressing the sense ING1 construct exhibited greater cell death (44% viability) suggesting that the ING1 gene confers cellular susceptibility to death induced by serum starvation.

Figure 13A:
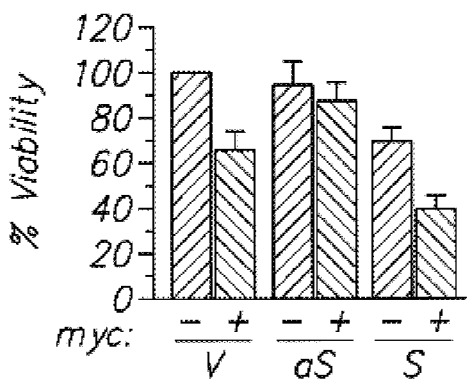
FIGS. 13A–13C illustrates that expression of ING1 enhances c-myc-induced apoptosis.

When c-myc was induced in the NIH 3T3 cells by tetracycline withdrawal and the cells were serum starved for 72 hours, they showed a viability of 65% compared with controls where myc was not induced (FIG. 13A). Apoptosis was minimized in cells coexpressing the antisense ING1 construct with only 5% of cells dying upon serum withdrawal. Cells expressing the ING1 protein alone showed 70% viability after serum starvation and apoptosis was magnified when c-myc was also expressed (40% viable). This showed that with both P19 and NIH 3T3 tet-myc cells expression of the ING1 gene is involved in regulation of apoptosis in a manner that is synergistic with the action of the myc gene.

Without being restricted to a theory, it appears that a loss of $p33^{ING1}$ or its function appears to have similar consequences to those observed for p53 (33, 34). Since ING1 appears to be important in the control of the G1 to S phase transition, it is possible that ING1 could modulate or be modulated by p53. Conversely, ING1 could act independently, perhaps providing an activity where p53-independent mechanisms are at work. Alterations in the proper functioning of $p33^{ING1}$ may contribute to tumorigenesis by rendering cells refractory to normal apoptotic pathways.

It is expected that several $p33^{ING1}$-related peptides will be useful in the present invention. In particular, $p33^{ING1}$, its analogs and related proteins and peptides which are effective in potentiating apoptosis in eukaryotic cells are preferred.

Included within the scope of the $p33^{ING1}$, as that term is used herein, are $p33^{ING1}$s having the amino acid sequence set forth in FIGS. 2 and 3, homologous amino acid sequence variants of the sequence of FIGS. 2 and 3, and homologous in vitro-generated variants and derivatives of $p33^{ING1}$, which are capable of exhibiting a biological activity in common with the $p33^{ING1}$ of FIG. 3. Also included are $p33^{ING1}$ variants having post-translational modifications, such as acetylation, glycosylation or phosphorylation.

$p33^{ING1}$ biological activity is defined as the possession of at least one cell proliferation, cell regulatory or tumor suppressive function qualitatively in common with native $p33^{ING1}$s. One example of the qualitative biological activity of $p33^{ING1}$ is its ability to inhibit cell growth as estimated by decreasing the S-phase fraction in a population of cells.

The effective quantity of $p33^{ING1}$ biological activity is that level of $p33^{ING1}$ biological activity necessary to potentiate apoptosis. The methods of this invention may reduce the effective quantity to less than 50% of the $p33^{ING1}$ biological activity of normal cells more preferably less than 30% of the $p33^{ING1}$ biological activity, most preferably there will be no $p33^{ING1}$ biological activity.

$p33^{ING1}$ immunological activity is defined herein as the possession of immunological cross-reactivity with at least one epitope of native $p33^{ING1}$. Immunologically cross-reactive, as used herein, means that the candidate polypeptide is capable of competitively inhibiting the qualitative biological activity of the native $p33^{ING1}$ having this activity, with polyclonal antisera raised against the known active analog. Such antisera are prepared in conventional fashion by injecting goats or rabbits, for example, subcutaneously with the known active analog in complete Freund's adjuvant, followed by booster intraperitoneal or subcutaneous injection in incomplete Freunds.

This invention is concerned with amino acid sequence variants of native $p33^{ING1}$. Amino acid sequence variants of the $p33^{ING1}$ are prepared with various objectives in mind, including increasing the affinity of the $p33^{ING1}$ for its binding partner, facilitating the stability, purification and preparation of the $p33^{ING1}$, modifying its biological half-life, improving therapeutic efficacy, and lessening the severity or occurrence of side effects during therapeutic use of the $p33^{ING1}$.

Amino acid sequence variants of $p33^{ING1}$ fall into one or more of three classes: insertional, substitutional, or deletional variants including those variations that arise from variable splicing of transcripts from the chromosomal gene. Additional variants may also be prepared by site specific mutagenesis of nucleotides in the DNA encoding the $p33^{ING1}$, by which DNA encoding the variant is obtained, and thereafter expressing the DNA in recombinant cell culture. However, variant $p33^{ING1}$ fragments having up to about 100 to 150 amino acid residues are prepared conveniently by in vitro synthesis.

The amino acid sequence variants of the $p33^{ING1}$ may be predetermined variants not found in nature or naturally occurring alleles. The $p33^{ING1}$ variants typically exhibit the same qualitative biological activity as naturally occurring $p33^{ING1}$. However, the $p33^{ING1}$ variants and derivatives that are not capable of exhibiting qualitative biological activity similar to native $p33^{ING1}$, may nonetheless be useful as reagents in diagnostic assays for $p33^{ING1}$ or antibodies to $p33^{ING1}$. Further, when insolubilized in accordance with known methods, they may be used as agents for purifying anti-$p33^{ING1}$ antibodies from antisera or hybridoma culture supernatants. Further, they may be used as immunogens for raising antibodies to $p33^{ING1}$ or as a component in an immunoassay kit (labeled so as to be a competitive reagent for native $p33^{ING1}$ or unlabeled so as to be used as a standard for the $p33^{ING1}$ assay) so long as at least one $p33^{ING1}$ epitope remains active in these analogs.

While the site for introducing an amino acid variation may be predetermined, the mutation, per se, need not be predetermined. For example, in order to optimize the performance of a mutation at a given site, random or saturation mutagenesis (where all 20 possible residues are inserted) is conducted at the target codon and the expressed $p33^{ING1}$ variant is screened for the optimal combination of desired activities. Such screening is within the ordinary skill of the art.

Amino acid insertions will usually be on the order of from about one to about ten amino acid residues; substitutions are typically introduced for single residues and deletions will range from about one to about thirty residues. Deletions or insertions preferably are made in adjacent pairs. That is, a deletion of two residues or insertion of two residues. Substitutions, deletions, insertions or any combination thereof may be introduced or combined to arrive at a final construct.

Insertional amino acid sequence variants of the native $p33^{ING1}$ are those in which one or more amino acid residues extraneous to native $p33^{ING1}$ are introduced into a predetermined site in the target $p33^{ING1}$ and which displace the pre-existing residues. Commonly, insertional variants are fusions of heterologous proteins or polypeptides to the amino or carboxyl terminus of the $p33^{ING1}$. Such variants are referred to as fusions of the $p33^{ING1}$ and a polypeptide containing a sequence which is other than that which is normally found in the $p33^{ING1}$ at the inserted position. Several groups of fusions are contemplated for carrying out the invention described herein.

Immunologically active $p33^{ING1}$ derivatives and fusions comprise the $p33^{ING1}$ and a polypeptide containing a non-p33$^{ING1}$ epitope. Such immunologically active derivatives and fusions of p33$^{ING1}$ are within the scope of this invention. The non-p33$^{ING1}$ epitope may be any immunologically competent polypeptide, i.e., any polypeptide which is capable of eliciting an immune response in the animal in which the fusion is to be administered, or which is capable of being bound by an antibody raised against the non-p33$^{ING1}$ polypeptide.

Substitutional variants are those in which at least one residue in the FIG. 3 sequence has been removed and a different residue inserted in its place. Novel amino acid sequences as well as isosteric analogs (amino acid or otherwise) are included within the scope of this invention.

Some deletions, insertions and substitutions will not produce radical changes in the characteristics in the p33$^{ING1}$ molecule. However, while it is difficult to predict the exact effect of the substitution, deletion or insertion in advance of doing so, for example, when modifying an immune epitope on the p33$^{ING1}$ protein, one skilled in the art will appreciate that the effect will be evaluated by routine screening assays. For example, a change in the immunological character of the p33$^{ING1}$ protein, such as affinity for a given antibody, is measured by a competitive-type immunoassay. Modifications of protein properties such as redox or thermal stability, hydrophobicity, susceptibility to proteolytic degradation, or the tendency to aggregate with carriers or into multimers may be assayed by methods well known to one of skill in the art.

Deletions of cysteine or other labile amino acid residues may also be desirable. For example, they may increase the oxidative stability of the p33$^{ING1}$ protein. Deletion or substitution of potential proteolysis sites, e.g., Arg Arg, is accomplished by deleting one of the basic residues or substituting one with glutaminyl or histidyl residues.

Covalent modifications of the p33$^{ING1}$ protein are included within the scope of the present invention. Such modifications are introduced by reacting targeted amino acid residues with an organic derivatizing agent that is capable of reacting with selected side chains or terminal amino acid residues. The resulting covalent derivatives of p33$^{ING1}$ are useful to identify residues important for p33$^{ING1}$'s biological activity, for immunoassays of the p33$^{ING1}$ or for preparation of anti-p33$^{ING1}$ antibodies for immuno-affinity purification of recombinant p33$^{ING1}$. Such modifications are within the ordinary skill of the art and are performed without undue experimentation.

In general, prokaryotes are used for cloning of DNA sequences and in constructing the vectors useful in the present invention. For example, E. coli HB101, DH5α and XL1-blue are particularly useful. These examples are meant to be illustrative and do not limit the present invention. Alternatively, in vitro methods of cloning such as the polymerase chain reaction may be used.

Expression hosts typically are transformed with DNA encoding the p33$^{ING1}$ protein which has been ligated into an expression vector. Such vectors ordinarily carry a replication site, although this is not necessary where chromosomal integration will occur. Expression vectors may also include marker sequences which are capable of providing phenotypic selection in transformed cells. Expression vectors also optimally will contain sequences which are useful for the control of transcription and translation.

Expression vectors used in eukaryotic host cells will also contain sequences necessary for the termination of transcription which may affect mRNA expression. Expression vectors may contain a selection gene as a selectable marker. Examples of suitable selectable markers for eukaryotic cells are dihydrofolate reductase, thymidine kinase, neomycin or hygromycin.

Antibodies to p33$^{ING1}$ may be prepared in conventional fashion [18] by injecting goats or rabbits, for example, subcutaneously with the complete p33$^{ING1}$ protein or a peptide consisting of at least 10 amino acids similar to the p33$^{ING1}$ protein in complete Freund's adjuvant, followed by booster intraperitoneal or subcutaneous injection in incomplete Freund's adjuvant, The anti-p33$^{ING1}$ antibodies may be directed against one or more epitopes on p33$^{ING1}$. Monoclonal antibodies against p33$^{ING1}$ can be prepared by methods known in the art [18]. The antibodies are preferably labelled with a marker, for example, with a radioactive or fluorescent marker. It is contemplated that the antibodies would be labelled indirectly by binding them to an anti-goat or anti-rabbit antibody covalently bound to a marker compound.

C. Pharmaceutical Compositions

The present invention may be used to potentiate apoptosis in eukaryotic cells by increasing expression of p33$^{ING1}$. For example, the potential for apoptosis is increased by introducing into cells a drug or other agent which can increase, directly or indirectly, expression of p33$^{ING1}$. Inducing apoptosis in cancer cells is of obvious importance. Inducing apoptosis in tissue culture cells provides a model system for studying the effects of certain drugs for triggering, reversing or halting the apoptotic pathway. Accordingly, increasing a cell's potential to enter the apoptotic pathway is useful.

In one embodiment, a protein or a peptide having p33$^{ING1}$ biological activity is introduced directly. In a preferred embodiment the peptide possesses at least apoptosis modulating function qualitatively in common with native p33$^{ING1}$.

In another embodiment nucleotides coding for p33$^{ING1}$ are introduced by retroviral or other means. In one embodiment the nucleotide coding for p33$^{ING1}$ comprises a nucleotide sequence which codes for a peptide having p33$^{ING1}$ biological activity. In one embodiment the oligonucleotide comprises an oligonucleotide which codes for the amino acid sequence set forth in FIG. 3. In another embodiment the oligonucleotide sequence comprises a nucleotide sequence which codes for the amino acid sequence set forth in FIG. 2. Preferably the nucleotide sequence is substantially identical to the cDNA sequence of FIG. 3, more preferably the sequence is substantially identical to the cDNA sequence of FIG. 2 and most preferably the sequence is substantially identical to nucleotides 161 to 1143 of the cDNA sequence of FIG. 3.

Apoptosis is inhibited or substantially decreased by preventing transcription of ING1 DNA and/or translation of RNA. This can be carried out by introducing antisense oligonucleotides of the ING1 sequence into cells, in which they hybridize to the p33$^{ING1}$-encoding mRNA sequences, preventing their further processing. It is contemplated that the antisense oligonucleotide can be introduced into the cells by introducing antisense single-stranded nucleic acid which is substantially identical to the complement of the cDNA sequence in FIGS. 2 or 3. It is also contemplated that an antisense oligonucleotide can be expressed in the cells by introducing a single- or double-stranded polynucleotide into the cell under conditions wherein a single-stranded nucleic acid sequence which is substantially identical to the complement of the cDNA sequence in FIGS. 2 or 3 is expressed in the cell, for example, by placing the polynucleotide in the antisense direction under the control of a strong promoter. It is contemplated that the antisense oligonucleotide introduced to the cell or expressed in the cell is at least 20 nucleotides, more preferably it is at least 50 nucleotides and most preferably it is at least 100 nucleotides in length. Preferably the antisense oligonucleotide sequence is substantially identical to the complement of nucleotides 942 to 1124 of the cDNA sequence set forth in FIG. 3.

It is also possible to inhibit expression of p33$^{ING1}$ by the addition of agents which degrade p33$^{ING1}$. Such agents include a protease or other substance which enhances p33$^{ING1}$ breakdown in cells. In either case the effect is indirect, in that less p33$^{ING1}$ is available than would otherwise be the case.

It is also possible to inhibit expression of p33$^{ING1}$ by inactivating the gene coding for ING1 in the cell. Such inactivation can occur by deleting the gene in the cell or by introducing a deletion or mutation into the gene thereby inactivating the gene. The gene may also be inactivated by inserting into the gene another DNA fragment such that expression of the native p33$^{ING1}$ protein does not occur. Methods for introducing mutations, deletions and insertions into genes in eukaryotic cells are known in the art. See, for example, U.S. Pat. No. 5,464,764 which is incorporated herein in its entirety.

It is contemplated that the ability to inhibit apoptosis in a eukaryotic cell in tissue culture provides a model system for testing certain proteins and factors for their role in the apoptotic pathway. It also provides a model system for testing compounds suspected of being tumorigenic.

Viral or plasmid vectors may be used to deliver various constructs to target cells in vitro or in vivo. Such viral vectors may include retroviruses, adenovirus or adenovirus-associated viruses. Such methods are known in the art [19].

In vitro such peptides or vectors may be administered by infection, microinjection, electroporation and by other methods known in the art.

In vivo parenteral administration of the nucleic acids is preferred with subdermal or intramuscular administration most preferred. Intravenous administration or use of implanted milliosmol pumps (available from Alza) may also be used.

When used for parenteral administration, which is preferred, the nucleic acids of the present invention may be formulated in a variety of ways. Aqueous solutions of the nucleic acids of the present invention may be encapsulated in polymeric beads, liposomes, nanoparticles or other injectable depot formulations known to those of skill in the art. (Examples thereof may be found, for example, in Remington's Pharmaceutical Sciences, 18th Edition, 1990.) The nucleic acids may also be encapsulated in a viral coat. Doses are selected to provide effective inhibition of cancer cell growth and/or proliferation.

The methods of this invention may also be achieved by using a pharmaceutical composition comprising one or more of the following apoptosis inducing compounds: p33$^{ING1}$, its analogs and related proteins and peptides. Doses are selected to provide effective induction of apoptosis.

Parenteral administration of the proteins or peptides is preferred, with subdermal or intramuscular administration most preferred. Intravenous administration or use of implanted milliosmol pumps (available from Alza) may also be used.

When used for parenteral administration, which is preferred, the proteins and peptides of the present invention may be formulated in a variety of ways. Aqueous solutions of the proteins or peptides of the present invention may be encapsulated in polymeric beads, liposomes, nanoparticles or other injectable depot formulations known to those of skill in the art. (Examples thereof may be found, for example, in Remington's Pharmaceutical Sciences, 18th Edition, 1990.)

Compositions including a liquid pharmaceutically inert carrier such as water may also be considered for both parenteral and oral administration. Other pharmaceutically compatible liquids may also be used. The use of such liquids is well known to those of skill in the art. (Examples thereof may be found, for example, in Remington's Pharmaceutical Sciences, 18th Edition, 1990.)

The dose level and schedule of administration may vary depending on the particular p33$^{ING1}$-related compound(s) and/or compositions used, the method of administration, and such factors as the age and condition of the subject.

As discussed previously, parenteral administration is preferred, but formulations may also be considered for other means of administration such as orally, per rectum, and transdermally. The usefulness of these formulations may depend on the particular compound used and the particular subject receiving the p33$^{ING1}$-related compound.

Oral formulations of p33$^{ING1}$-related compounds may optionally and conveniently be used in compositions containing a pharmaceutically inert carrier, including conventional solid carriers, which are conveniently presented in tablet or capsule form. Formulations for rectal or transdermal use may contain a liquid carrier that may be oily, aqueous, emulsified or contain certain solvents suitable to the mode of administration. Suitable formulations are known to those of skill in the art. (Examples thereof may be found, for example, in Remington's Pharmaceutical Sciences, 18th Edition, 1990.)

D. Use of ING1 DNA and RNA and p33$^{ING1}$ and Related Proteins and Peptides for Diagnosis The present invention also has diagnostic use, since simple immunochemical staining of cells or sections of cells should give an accurate estimate of the portion of cells expressing p33$^{ING1}$. Such a test based on the use of anti-p33$^{ING1}$ antibodies or ING1 polynucleotides and other standard secondary techniques of visualization will be useful in determining the apoptotic characteristic of eukaryotic cells. Such a test might also be useful to the scientific research community.

Antibodies specifically reactive with p33$^{ING1}$ can be produced, using known methods [18]. For example, anti-p33$^{ING1}$ antisera can be produced by injecting an appropriate host (e.g., rabbits, mice, rats, pigs) with p33$^{ING1}$ and withdrawing blood from the host animal after sufficient time for antibodies to have been formed. Monoclonal antibodies can also be produced using known techniques [18]. Such antibodies to p33$^{ING1}$ will generally be detectably labelled (e.g., with a radioactive label, a fluorescent material, biotin or another member of a binding pair or an enzyme) by methods known in the art. It is also contemplated that the anti-p33$^{ING1}$ antibodies may be indirectly labelled as follows. The unlabelled primary antibody binds to the target protein. Then a secondary antibody (anti-antibody) directed against the primary antibody and tagged with a detectable label binds to the antigen-primary antibody complex.

In a diagnostic method of the present invention, cells obtained from an individual or a culture are processed in order to determine the extent to which p33$^{ING1}$ is present in cells, in a specific cell type or in a body fluid. This can be determined using known techniques and an antibody specific for p33$^{ING1}$. Comparison of results obtained from cells or a body fluid being analyzed with results obtained from an appropriate control (e.g., cells of the same type known to have normal p33$^{ING1}$ levels or the same body fluid obtained from an individual known to have normal p33$^{ING1}$ levels) is carried out. Decreased p33$^{ING1}$ levels are indicative of an increased probability of abnormal cell proliferation or oncogenesis or of the actual occurrence of abnormal proliferation or oncogenesis. It is contemplated that the levels of p33$^{ING1}$ in cancerous cells will be at least 50% less than the level of p33$^{ING1}$ in non-cancerous cells, more preferably the levels will be less than 30% of normal levels, most preferably p33$^{ING1}$ will not be expressed. Increased p33$^{ING1}$ levels are indicative of an increased probability that the cell is capable of entering the apoptotic pathway. It is contemplated that the levels of p33$^{ING1}$ in apoptotic cells will be at least 50% greater than the level of p33$^{ING1}$ in normal cells, more preferably at least 70% greater.

It is contemplated that a diagnostic kit could include a solid support for attaching the cell or tissue to be tested and a detectably labelled anti-p33$^{ING1}$ antibody. It is further contemplated that the anti-p33$^{ING1}$ antibody may not be labelled but the kit would additionally contain another detectably labelled antibody capable of binding to the anti-p33$^{ING1}$ antibody.

A hybridization probe comprising RNA, ING1 cDNA or ING1 genomic DNA having a sequence substantially identical to FIG. 3 ("ING1 polynucleotide") may be employed as a means for determining the sequence of the ING1 gene present in the genomic DNA of a given sample, or the level of ING1 mRNA expressed in cells of such sample. Such hybridization probes will generally be detectably labelled (e.g. with a radioactive label, a fluorescent label, biotin, etc). It is also contemplated that the ING1 polynucleotide may be indirectly labelled by methods known in the art. It is contemplated that in situ hybridization of labelled nucleic acid to the cell will be employed to detect the presence of ING1 mRNA in the cell.

A tissue sample or cell sample can be prepared by conventional means and probed with the labelled ING1 polynucleotide probe to determine the level of expression of ING1 mRNA in the cells. The ING1 polynucleotide probe may also be used to determine whether the genomic DNA from the cell sample has a mutation or rearrangement of its ING1 gene by methods known in the art (i.e. PCR sequencing or restriction fragment length polymorphism analysis). The polynucleotide probe may also be used to determine whether the genomic DNA from the cell sample has a mutation/deletion rearrangement of the chromosome region of 13q33-34.

The oligonucleotide probe useful in these methods may comprise at least about 20 nucleotides which sequence is substantially identical to the sequence of FIG. 3, more preferably it will comprise at least about 100 nucleotides, and most preferably it will comprise at least 400 nucleotides. In the case of PCR sequencing it is contemplated that one of the two ING1 oligonucleotide primers will be substantially identical to one region of the sequence of FIG. 3 and that the second oligonucleotide primer will be substantially identical to the complement of a second region of the sequence of FIG. 3. The size of these primers is preferably from 15–25 nucleotides, more preferably from 15–20 nucleotides. Most preferably the oligonucleotide probes and primers will be substantially identical to the coding region of the cDNA sequence of FIG. 3. Such nucleotides can be generated synthetically by conventional means.

Comparison of the results obtained from cells or a body fluid being analyzed with results obtained from an appropriate control (e.g. cells of the same type known to have abnormal or native p33$^{ING1}$ or fluid from an individual known to have normal p33$^{ING1}$) is carried out. Decreased ING1 mRNA levels are indicative of an increased probability of abnormal cell proliferation or oncogenesis or of the actual occurrence of abnormal proliferation or oncogenesis. It is contemplated that the levels of ING1 mRNA in cancerous cells will be at least 50% less than the level of ING1 mRNA in non-cancerous cells, more preferably the levels will be less than 30% of normal levels, most preferably ING1 mRNA will not be expressed. Increased ING1 mRNA levels are indicative of an increased probability of cell apoptosis. It is contemplated that the levels of ING1 mRNA in cells having apoptotic potential will be at least 50% more than the level of ING1 mRNA in native non-senescent cells, more preferably at least 70% more than native non-senescent cells.

The presence of a mutation/deletion in one copy of the ING1 gene in a diploid cell is also indicative of an increased probability that abnormal cell proliferation will occur. The presence of mutations/deletions in both copies of the ING1 gene is indicative of possible or actual oncogenesis.

The following examples are offered to illustrate this invention and are not meant to be construed in any way as limiting the scope of this invention.

EXAMPLES

The methods described as follows were used to perform the studies described herein. In addition, the generally known methods set forth in laboratory manuals for molecular cloning and antibody techniques [e.g., 17,18] may advantageously be used by one of skill in the art to produce additional embodiments of the invention.

Example 1
Strategy for Cloning and Biological Assays

Subtractive hybridization of breast cancer cell line cDNAs with cDNA from normal mammary epithelial cells, subcloning of subtracted cDNAs into the pLNCX retroviral vector [7] and injection into nude mice was done essentially as described [3] with the modifications noted below. The cloning of full length cDNA was done using standard methods [17]. The strategy is shown in FIG. 1A.

cDNA was prepared from an non-transformed mammary epithelial cell line (184A1) [6] and digested with the restriction enzyme Sau3A. cDNAs from the breast cancer cell lines MCF-7, BT-483, BT-474, Hs-578T, ZR-75, MD-MB-468, MD-MB-435 and BT-20 (obtained from the American Type Culture Collection, Bethesda, Md.) were also digested with Sau3A. Fragments of tester DNA (cDNA from normal epithelial cells) were ligated to "a" adaptors. Fragments of driver DNA (cDNA from breast tumor cells) were ligated to "b" adaptors. Adaptors were prepared by annealing the synthetic oligonucleotides:

5'-GACCTGGCTCTAGAATTCACGACA-3' (SEQ ID NO: 3) with

5'-GATCTGTCGTGAATTCTAGAGCCAGG-3' (SEQ ID NO: 4) (adaptor "a"); and

5'-GACTCGACGTTGTAACACGGCAGT-3' (SEQ ID NO: 5) with

5'- GATCACTGCCGTGTTACAACGTCGAG-3' (SEQ ID NO: 6) (adaptor "b").

The mixture of driver DNA and tester DNA was denatured, then hybridized at 66° C. for 18 hours. After hybridization, mixtures were treated with Mung bean nuclease to eliminate single-stranded adaptor-derived ends from "heterozygous" hybrids (hybrids containing both a and b adaptors). Resultant double-stranded molecules were then selectively amplified by PCR using primer "a".

The "amplicons" were then subjected to five successive rounds of hybridization, selective degradation and PCR amplification using 40 μg of driver cDNA containing adaptors and 200 ng, 5 ng and 5 pg of tester amplicons in respective rounds. This procedure allowed for a significant enrichment of sequences that were more highly expressed in the phenotypically normal epithelial cells as determined by slot blot hybridization.

All subtracted fractions were combined and used as a probe to screen a near-senescent human diploid fibroblast cDNA library. Following screening, 300 cDNA clones were isolated and their inserts were randomly fragmented (200–800 bps). These were then ligated with adaptors prepared by annealing two oligonucleotides
5'-AATCATCGATGGATGGATGG-3' (sense) (SEQ ID NO: 22)
5'-CCATCCATCCATCGATGATTAAA-3' (SEQ ID NO: 23) and
were amplified by PCR using the "sense" strand of the adaptor as the PCR primer. PCR amplified DNA was recloned into the ClaI site of the retroviral plasmid vector pLNCX [7] with synthetic adaptors carrying initiation codons in all reading frames. This library of about $10^5$ clones, enriched in tumor suppressor sequences was then used for the isolation of transforming genetic suppressor elements (GSEs).

After transfection of the recombinant retroviral plasmids into the packaging line BOSC 23 [25], retroviruses containing the isolated cDNA fragments were used to infect non-tumorigenic immortalized mouse mammary epithelial cells (NMuMG) which were subsequently injected subcutaneously into nude mice. Subcloning into the retroviral vector, packaging into the BOSC 23 virus-packaging cell line and assays using nude mice were performed as described [3].

After 45 days, two mice developed tumors from which two cDNA inserts were recovered by PCR, one of which is subsequently shown to be expressed in the antisense orientation. The primers used in the PCR amplification were:
5'-CCAAGCTTTGTTTACATCGATGGATG-3' (SEQ ID NO: 7) (sense); and
5'-ATGGCGTTAACTTAAGCTAGCTTGCCAAACCTAC-3' (SEQ ID NO: 8)
(antisense). The recovered cDNA insert which was in the antisense orientation was digested with ClaI and HindIII and recloned back into the retroviral vector, pLNCX, in the same position and orientation and then tested individually in vitro.

NMuMG cells were infected with retrovirus produced from pLNCX vector containing or not containing the ING1 insert (nucleotides 942 to 1,124 of the ING cDNA set forth in FIG. 3). The soft agar culture was comprised of two layers: an underlay (DMEM, 10% FCS, 0.6% agar) and an overlay (DMEM, 10% FCS, 0.3% agar). $5\times10^4$ cells were plated in soft agar in 10 cm plates and were left at 37° C. for 6–7 weeks before being counted. $5\times10^5$ transfected NIH 3T3 cells were plated per 10 cm dish. Transfected NIH 3T3 cells were grown in 5% serum for 4 weeks prior to fixing and visualizing foci. pLNCX-S and pLNCX-αS represent sense and antisense orientations of the ING1 cDNA insert, respectively.

TABLE 1

Results of the soft agar and focus forming assays.

| Trial Number | Soft agar assay | | | | | Focus forming assay | | |
|---|---|---|---|---|---|---|---|---|
| | 1 | 2 | 3 | 4 | mean | 1 | 2 | mean |
| pLNCX (vector) | 0 | 0 | 0 | 0 | 0 | 9 | 13 | 11 |
| pLNCX-Ras | 224 | 248 | 208 | (—) | 226.7 | (—) | (—) | (—) |
| pLNCX-αS | 42 | 46 | 41 | 82 | 52.8 | 18 | 34 | 26 |
| pLNCX-S | (—) | (—) | 0 | 0 | 0 | (—) | (—) | (—) |

(—) = not determined

These results showed that the antisense ING1 cDNA insert caused increased cell proliferation.

Panel 1 of FIG. 1B shows NMuMG cells infected with the retroviral vector pLNCX and panel 2 of FIG. 1B shows cells infected with the retroviral vector pLNCX containing the antisense ING1 insert. The bar equals 1 mm. Panel 3 of FIG. 1B shows NIH 3T3 cells transfected with vector alone and panel 4 of FIG. 1B shows cells transfected in parallel with pLNCX containing the antisense ING1 insert.

Example 2 cDNA of ING1 and Predicted Amino Acid Sequence of $p33^{ING1}$

In order to isolate the gene corresponding to the fragment showing biological effects, normal human fibroblast and HeLa cell cDNA libraries were screened with the ING1 cDNA fragment from Example 1, resulting in the isolation of 11 positive clones. Two clones containing the largest cDNA inserts were sequenced on both strands using an Applied Biosystems automated sequencer, yielding the sequence shown in FIG. 2.

In order to obtain the 5' end of the ING1 gene, 5' RACE (rapid amplification of cDNA ends) was used. Total cDNAs isolated following reverse transcription had the synthetic adaptor
5'-GTACATATTGTCGTTAGAACGCGTAATACGCCTC-ACTATAGGGA-3' (SEQ ID NO: 11) ligated to them and PCR reactions using nested primers from both the adaptor and the ING1 gene were used to amplify the 5' ends of all RT-generated cDNAs. The primers used in the amplification were:
5'-CTGGATCTTCTCGTCGCC-3' (SEQ ID NO: 12) and
5'-AGTGCAGCATCGGCCGCTTC-3' (SEQ ID NO: 13) from the ING1 sequence and:
5'-GTACATATTGTCGTTAGAACGCG-3' (SEQ ID NO: 14) and
5'-TAATACGCCTCACTATAGGGA-3' (SEQ ID NO: 15) from the adaptor sequence. The largest PCR products were recovered from agarose gels following electrophoresis and were subcloned and sequenced to generate the full-length sequence shown in FIG. 3.

The predicted coding region of ING1 begins at nucleotide 16 and ends at nucleotide 898, as shown in FIG. 3, predicting a translation product of 33,350 daltons. Comparison of the sequence of $p33^{ING1}$ to the available protein and nucleotide data bases showed no significant homology to any sequence encoding a known protein and very limited similarity to retinoblastoma binding protein 2 (RbBP2) [9] and to several zinc finger transcription factors. Regions of the $p33^{ING1}$ protein that show homology to different members of the $p16^{MTS1}$ family of cyclin-dependent kinase inhibitors and to retinoblastoma binding protein 2 were identified using the Blast program available from the National Centre for Biological Information (address: www.ncbi.nimn.nih.gov).

Example 3
Expression of a GST-p33$^{ING1}$ fusion protein and creation of anti-p33 polyclonal antibody In order to generate polyclonal antibodies, a fragment of ING1 containing nucleotides 161–1146 of FIG. 3 was subcloned into the EcoRI-XhoI sites of the bacterial expression vector pGEX-4T1 (Pharmacia Biotech, Inc., Quebec, Canada) containing the glutathione-binding portion of glutathione-S-transferase (GST). Plasmids were sequenced to verify that the correct reading frame was obtained and the constructs were electroplated into E. coli XL1-Blue. Following selection, bacterial cultures were induced to express the fusion protein by the addition of 0.1 mM isopropyl thio-galactopyranoside (IPTG) and fusion protein was purified by standard glutathione-Agarose column affinity chromatography. Eluted GST-p33$^{ING1}$ fusion protein was dialyzed and used in immunogen in female New Zealand white rabbits. After four boosters, rabbits were bled and their serum tested for reactivity against the fusion protein. All animals showed reactivity and the bleeds showing the highest titer were chosen for subsequent use in Western blot, immunoprecipitation and immunofluorescence protocols.

Example 4
Effect of the antisense ING1 fragment on expression of p33$^{ING1}$ in tissue culture cells Analysis of p33$^{ING1}$ protein levels in cell samples was performed by Western blotting using anti-p33$^{ING1}$ antibodies raised against the GST-p33$^{ING1}$ fusion protein. Proteins were separated by electrophoresis in 12.5% polyacrylamide/SDS gels, and electrophoretically transferred to membranes for 1 hour. The membranes were blocked in TBS (100 mM Tris, 150 mM NaCl) containing 10% non-fat dried milk and 0.1% Tween-20, for 2 hours. Incubation of the membranes with p33$^{ING1}$ antiserum was performed in TBS containing 5% nonfat milk and 0.1% Tween 20 (TBST) for 30 minutes. Horseradish peroxidase-conjugated goat anti-rabbit antibody was then applied to the filters for 1 hour in TBST. Peroxidase activity was detected using a chemiluminescence system (Amersham Canada, Oakville Ontario Canada)

As shown in FIG. 1C, NMuMG (lane 1) and ZR-75 (lane 2) cell lines were tested. The Western blot analysis of human and mouse cell lysates revealed a protein of 33 kD. Preincubation of antibodies with GST-p33$^{ING1}$ fusion protein blocked recognition of p33$^{ING1}$ in a parallel blot using lysates from the same cells (lanes 3 and 4).

To determine whether the level of p33$^{ING1}$ was decreased in cells infected with viral constructs containing the antisense orientation, lysates were prepared from control NMuMG cells and from NMuMG cells infected with antisense ING1 (pLCNX-αS) that had grown and formed colonies in semi-solid medium. A Western blot of lysates from NMuMG cells infected with pLNCX vector (lane 5) or pLNCX vector containing antisense ING1 insert (lane 6) by the method set out above is shown in FIG. 1C. Results of the Western blot analysis showed that chronic expression of antisense construct reduced the expression of the endogenous ING1 gene by approximately 90% compared to control parental cells.

Example 5
Effects of p33$^{ING1}$ Overexpression

Isolation of a DNA fragment that was capable of inducing foci and growth in soft agar when expressed in the antisense orientation, suggested that the cellular role of ING1 might be to negatively regulate growth. To test this idea, part of the ING1 cDNA (basepairs 161 to 1143 of FIG. 3) was cloned into the mammalian expression vector pBK (Stratagene, Aurora, Ontario Canada) in the sense orientation (pING1-S). This construct and the plasmid vector, both of which contain neomycin resistance genes and a cytomegalovirus (CMV) promoter, were transfected into human breast cancer (Hs578T) and normal fibroblast (Hs68) cells. Following growth for 3 weeks in medium containing G418, plates were fixed and stained with Coomassie Brilliant Blue to identify surviving colonies. A large number of stable transformants were recovered from cells transfected with vector whereas very few colonies were visible in plates of cells transfected with the sense orientation of the cDNA of ING1. FIG. 4A shows the results when human Hs578T breast cancer cells (panels 1 and 2) and normal fibroblasts (panels 3 and 4) were transfected with the plasmids pBK (panels 1 and 3) or pING1-S containing the ING1 cDNA in the sense orientation (panels 2 and 4).

In order to corroborate the results of these chronic assays, we next examined the effect of microinjecting these constructs on the ability of normal diploid fibroblasts to initiate DNA synthesis.

Hs68 cells were plated on glass coverslips, deprived of serum for 12 hours, microinjected with the indicated mixture of plasmid DNA (0.1 μg/ml) plus nonspecific IgG (2 μg/ml) and were then incubated for 36 hours in complete medium containing BrdU. Fixed cells were identified by staining for injected IgG and for the incorporation of BrdU. Microinjection, fixation and staining were done as described previously [16].

FIG. 4C shows the combined results of 5 separate experiments. Each group represents 110–200 injected cells. As shown in FIG. 4B, normal Hs68 HDFs were injected with solutions containing pING1-S plus non-specific rabbit IgG (panels 1 and 2) or with pING1-αS containing the ING1 cDNA in the antisense orientation plus non-specific rabbit IgG (panels 3 and 4). Injected cells were grown in the presence of BrdU and were fixed and stained for the presence of co-injected IgG (panels 1 and 3) or incorporated BrdU (panels 2 and 4). Arrows identify injected cells. Arrows in panels 2 and 4 show that cells injected with pING1-S failed to incorporate bromodeoxyuridine (BrdU, panel 2) over a 36 hour time course after injection, whereas those injected with pING1-αS entered S phase (panel 4) as estimated by staining with anti-BrdU antibodies. FIG. 4C shows the results of 5 separate experiments which indicate that injection of the pBK vector or of pING1-αS constructs had no appreciable effect upon the ability of cells to proceed through S phase.

Similar results were obtained in larger populations of cells that were electroporated with vector, sense and antisense construct DNAs together with a construct encoding the CD20 surface marker. Such co-transfections allowed the analysis by flow cytometry of DNA content in transfected cells that were positive for CD20 staining. Hs68 cells were co-transfected with pCMV-CD20 together with pBK-p33$^{ING1}$-S or with pBK vector as a negative control. Cells were fixed and stained for CD20 expression using commercially available antibodies and with propidium iodide 48 hours after electroporation. Cell cycle distribution was determined by flow cytometry using fluorescence-activated cell sorting. The percentage of the CD20+ cells in different phases of the cell cycle is shown for two independent experiments.

TABLE 2

Overexpression of p33$^{ING1}$ arrested cells in G0/G1

| | pBK (vector) | | | pBK-ING1-S | | |
|---|---|---|---|---|---|---|
| | G1/G0 | S | G2/M | G1/G0 | S | G2/M |
| Trial 1 | 32.7 | 38.5 | 28.8 | 53.3 | 19.9 | 26.8 |
| Trial 2 | 34.5 | 35.9 | 29.6 | 72.8 | 19.7 | 7.5 |
| mean | 33.6 | 37.2 | 29.2 | 63.1 | 19.8 | 17.2 |

As shown in Table 2, the CD20-expressing population that was cotransfected with pING1-S had, on average, 63.1% of cells in G0/G1 whereas those co-transfected with vector had 33.6% of cells in G0/G1 when cells were fixed and stained 48 hours after electroporation. These results, using several independent methods, indicate that the overexpression of ING1 inhibits cell growth in both transient and chronic assays, most likely be arresting cells in the G1 phase of the cell cycle.

Example 6
Alterations of ING1 in cancer cell lines

Since ING1 was originally isolated by subtractive hybridization between normal and transformed epithelial cDNAs, the ING1 gene and its expression in breast cancer cell lines was also examined. In FIG. 5A, lane 1 is MCFIOA phenotypically normal epithelial cell line from mammary gland; lane 2 is MDA-MB-468; lane 3 is ZR-75; lane 4 is BT-20; lane 5 is SK-BR-3; lane 6 is MCFT; lane 7 is Hs578T and lane 8 is BT-474 (breast cancer cell lines). FIG. 5B shows the coomassie-blue stained gel corresponding to FIG. 5A. The expression of p33$^{ING1}$ in the cell lines was tested by preparing lysates of cell lines and Western blotting using anti-p33$^{ING1}$ antibodies by the method in Example 4. Although analysis of genomic fragments containing the ING1 gene did not reveal any structural changes in breast cell lines, results from Western blot analyses shown in FIG. 5 suggest that the p33$^{ING1}$ protein was expressed at considerably lower levels in some breast cancer cells compared to a phenotypically normal epithelial cell line. This observation of reduced expression in the absence of mutation is similar to the expression of BRCA-1 reported to occur in non-hereditary forms of breast cancer [25].

Normal diploid control cell strains and neuroblastoma cell lines were analyzed by Western Blot analysis in a manner similar to that set forth for the breast cancer cell lines. FIG. 6A illustrates the Western blotting results of IMR-5 (lane 1) SK-L-C6 (lane 2); SK-N-SH (lane 3) all neuroblastoma cell lines, and W138 (lane 4) a normal diploid lung fibroblast cell line. Normal diploid fibroblast cells expressed low levels of p33$^{ING1}$ while immortalized neuroblastoma cells expressed considerably higher levels and in the case of the SK-N-SH neuroblastoma line a truncated protein was observed.

To investigate the nature of the change(s) responsible for truncating p33$^{ING1}$ in this neuroblastoma cell line, two complementary approaches were taken. Southern blot analysis of DNA, from neuroblastomas and from normal fibroblasts that was digested with different restriction endonucleases and probed with a ING1 nucleic acid probe, clearly indicated that p33$^{ING1}$ was rearranged in the neuroblastoma cell line. Human genomic DNAs were digested with HindIII, DraI or PstI, electrophoresed through a 0.7% agarose gel, transferred to a nitrocellulose membrane and hybridized with [$^{32}$P]-labelled p33$^{ING1}$ cDNA. Hybridization was performed using standard procedures [17]. Lanes 1–6 show the results for neuroblastoma SK-N-SH (2, 4 and 6) and for normal diploid W138 cells (1, 3 and 5). Patterns such as those shown by W138 cells were also seen in other normal diploid cell strains.

To confirm that changes in the p33$^{ING1}$ gene had occurred in the neuroblastoma cell line and to determine their nature by an independent method, reverse transcription polymerase chain reaction (RT-PCR) with RNA from SK-N-SH neuroblastoma cell line and from a phenotypically normal epithelial cell line (MCF-10) was performed as described [20]. Neuroblastoma cDNA was amplified with PCR primers specific for the p33 gene (direct(d) and reverse (r) primers). These are numbered and shown underlined in FIG. 3 and the PCR products were compared with PCR fragments generated in parallel from control cell cDNA. FIG. 6C, lanes 1 (primers 1d-4r), 3 (1d-2r), 5 (2d-4r) and 7 (2d-3r) show the results for W138, and lanes 2 (1d-4r), 4 (1d-2r), 6 (2d-4r) and 8 (2d-3r) show the results for the neuroblastoma cell line. Primers were 1d: GTAGCGCAGTCTGACAAGCC (nucleotides 474–494 of SEQ ID NO: 9)
2d: TGGTTCCACTTCTCGTGCGT (763–782 of SEQ ID NO: 9)
2r: ACGCACGAGAAGTGGAACCA (SEQ ID NO: 16)
3r: TTTGGATTTCTCCAGGGCTT (SEQ ID NO: 17) and
4r: TACCTGTTGTAAGCCCTCTC (SEQ ID NO: 18).

M shows a 1 kb ladder molecule weight marker. All primer pairs gave similar results in both cell lines except for those using primers beyond nucleotide 858. For example, using primers 3r and 4r give no PCR product using neuroblastoma cDNA which is consistent with data indicating that a deletion or a rearrangement had occurred within the p33$^{ING1}$ gene. These experiments corroborate the idea that the 3' region of the p33$^{ING1}$ gene was mutated in is neuroblastoma.

Figure 7:
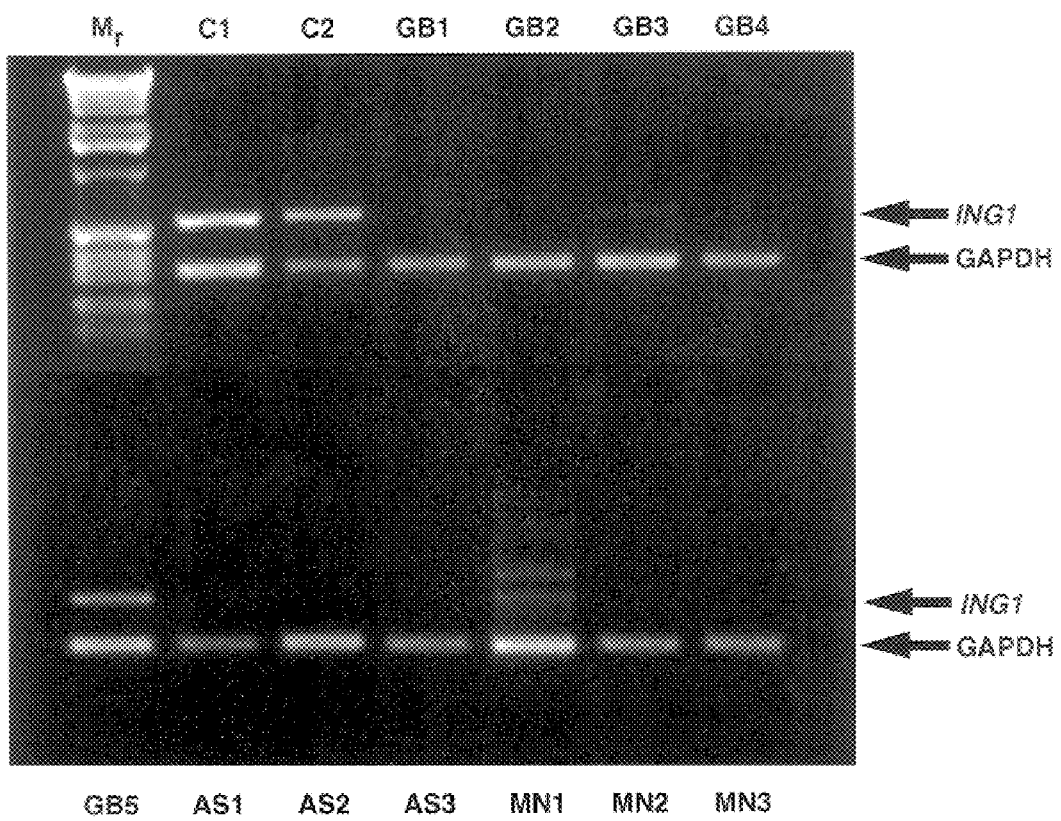
FIG. 7 illustrates the level of ING1 mRNA in control (c) tissue, glioblastoma (GB), astrocytoma (AS) and meningioma (MN) tumors as determined by RT-PCR.

Normal diploid control cell strains and brain cancer cell lines were analyzed by RT-PCR analysis. Reverse transcription with total RNA from each of the cell lines was performed by the method set out in Example 9. The same primer pairs set forth in Example 9 were used. FIG. 7 illustrates the RT-PCR results of glioblastoma (lanes GB1–GB4) astrocytoma (lanes AS1–AS3) and meningioma (MN1–MN3) as compared to a control cell line (C1–C2). The ING1 mRNA was expressed at considerably lower levels, or not expressed at all, in the glioblastomas, astrocytomas and meningiomas as compared to the normal cell line.

Example 7
Nuclear Localization of p33$^{ING1}$

The experiments described below were performed with a rabbit polyclonal antibody (αp33) which was raised against a bacterially expressed glutathione-S-transferase (GST)-p33$^{ING1}$ fusion protein and which reacted with a 33 kDa protein in human and mouse cell lysates as prepared by the method in Example 3.

In the first series of experiments, we determined the location of p33$^{ING1}$ in fibroblasts by examining the staining pattern of anti-p33 antibody in fibroblasts by indirect immunofluorescence. For indirect immunofluorescence normal human diploid fibroblasts (Hs68 cells) were grown on glass coverslips for 48 hours at 37° C. to 60% confluence. The cells were fixed in 3.7% formaldehyde, washed in 0.5% Triton X-100 and in 0.05% Tween 20 for 10 minutes each at room temperature. Formaldehyde and detergents were diluted in phosphate buffered saline (PBS) pH 7.5. The cells were incubated with a 1:100 dilution of rabbit p33$^{ING1}$ antiserum for 30 min, washed in PBS with 0.05% Tween, incubated with goat anti-rabbit IgG-biotin antibody and then with streptavidin conjugated Texas Red [16]. Samples were examined with a Zeiss Axiophot fluorescence microscope and images were photographed on Kodak TMAX 100 film.

Staining with polyclonal rabbit antibody alone was observed both in nuclear and cytoplasmic compartments. Similar results were obtained with anti-p33 antibodies which were preincubated with 5 μg of GST protein indicating that the signal was specific for p33$^{ING1}$. When the anti-p33 serum was preincubated with 5 μg of GSTp33 fusion protein, nuclear staining was lost completely but cytoplasmic staining remained, indicating that the vast majority of p33$^{ING1}$ staining was nuclear.

To confirm the nuclear localization of the 33 kDa protein. The pING1-s construct of Example 5 was microinjected into normal Hs68 fibroblast cells which were fixed and stained with anti-p33-antibody 24 hours after injection. Strong staining was clearly localized to the nucleus. These results corroborate staining patterns in uninjected cells and show that p33$^{ING1}$ is localized primarily, and possibly exclusively, throughout the nucleoplasm.

Example 8

Chromosomal Localization of the ING1 gene

To identify the chromosomal localization of the ING1 gene, a genomic 18-kb DNA insert containing the gene was labelled with digoxygenin-dUTP and hybridized to synchronized human lymphocyte metaphase spreads.

A genomic clone of the ING1 gene was isolated from a lambda FIX II placental human genomic library (Stratagene, Aurora, Ontario, Canada) with nucleotides 161 to 1143 of the ING1 sequence of FIG. 3 using high stringency (65° C. 0. 1X SSC, 0.1% SDS) screening. The identity of the clone was confirmed by partial sequence analysis.

FISH was performed using established methods on methotrexate/thymidine synchronized, phytohemagglutinin stimulated, normal peripheral blood lymphocytes [21]. Approximately 50 metaphase spreads were examined for probe localization. Suppression for 30 minutes with a mixture of sonicated human DNA (Sigma Diagnostics, Mississauga, Ontario, Canada) and cotl DNA (Gibco/BRL, Burlington, Ontario, Canada) was required to reduce the background. The stained slides were counterstained with DAPI and actinomycin D (for a DA-DAPI banding pattern) and were mounted in antifade medium and visualized utilizing a Zeiss Axioplan 2 microscope. Images of representative mitoses were captured using a cooled CCD camera (Photometrics PXL 1400). Digital alignment of the images from each fluor was done after registration calibration through a triple bandpass filter (FITC/Texas Red/DAPI) to minimize registration error, utilizing commercial software (Electronic Photography v1.3, Biological Detection Inc., Pittsburgh, Pa.).

The results clearly showed localization of the probe to chromosomal region 13q33-34. At least one specific probe signal was present in more than 90% of the mitoses examined. Approximately 80% of the cells had two chromatids of a single chromosome. Approximately, 40% showed labelling of both chromatids of both chromosomes. More than 90% of the signals were localized to a single band. In addition, cohybridization of p33$^{ING1}$ with a commercial 13/21 alpha-satellite probe (Oncor, Gaithersberg, Md.) showed hybridization to the same chromosome.

The ING1 gene has been localized to an area near known sites of genomic alteration in several human cancers: primary gastric cancer [22], hematologic neoplasms [23] and head and neck squamous cell carcinomas [24].

Example 9

Expression levels of ING1 in young and senescent fibroblasts

The normal human diploid fibroblast cell strain Hs68 (ATCC CRL#1635) and a phenotypically normal mouse epithelial cell line from mammary gland (NMuNG) were grown in Dulbecco's modified Eagle's medium (DMEM) containing 10% fetal bovine serum. Hs68 cells were used at 30 ("young"), 70 ("pre-aged") and 80 ("old") mean population doublings (MPDs) for expression and life span experiments. After retroviral infection, the human diploid fibroblast cells (HDFs) were repeatedly passaged in 10 cm plates, splitting at a ratio of 1:2 when confluent.

For infection of fibroblasts, the retroviral vector (pLNCX) was used. The highly efficient ecotropic (BOSC23) and amphotropic (CAK8) packaging cell lines were used [26]. pLNCX-αS or pLNCX alone, were transfected into the BOSC23 virus-packaging cell line. Ecotropic and amphotropic packaging lines, and the retroviral vector were kindly provided by Dr. A. Gudkov (University of Illinois at Chicago). The amphotropic cells were infected by viruses from the BOSC23 supernatant. Fibroblasts were plated at $10^5$ cells per 10 cm plate and infected with undiluted viral supernatant from amphotropic producer cells. Infection efficiencies ranged from 85 to 95% in individual trials.

Since the activity or expression levels of several tumor suppressors increase in senescent cells, the levels of ING1 expression in low and high passage cells were checked. All experiments were performed on the Hs68 strain of primary normal human diploid fibroblasts. Senescent cells were obtained by passaging early-passage ("young") fibroblasts continuously to a point at which one population doubling required from 2–3 weeks to complete compared to 24 hours, on average, for young HDFs. Hs68s at 80 MPDs exhibited characteristics typical of senescent cells, including an inability to respond to growth factors and altered morphology including increased size and decreased saturation density.

To study the level of expression of ING1 mRNA, RT-PCR using total RNA isolated from young and old cells was performed (FIG. 8A). The relative levels of ING1 transcript were compared to the internal control gene glyceraldehyde-3-phosphate dehydrogenase (GAPDH) using PCR primers specific for the p33 and GAPDH genes. ING1 and GAPDH were amplified in the same reaction tube using the "primer dropping" approach [27] which internally controls for efficiency of reverse transcription and amplification by PCR.

Reverse transcription (RT) with 1 μg of total RNA from young and old Hs68 cells was performed using 50 U of RNasin (Pharmacia Biotech, Inc., Quebec Canada) and 200 U of MMLV reverse transcriptase for 50 min. at 42° C. in 20 μl reaction volumes. Two μl of each RT reaction was amplified using 2 U of Taq polymerase. The two sets of primer pairs for the ING1 gene and for the GAPDH gene that were used, were:

5'-GAAGCGGCGGATGCTGCACT-3' (SEQ ID NO: 19); and

5'-ACGCACGAGAAGTGGAACCA-3' (SEQ ID NO: 16) for the ING1 gene and

5' CGGAGTCAACGGATTTGGTCGTAT-3' (SEQ ID NO: 20); and

5'-AGCCTTCTCCATGGTGGTGAAGAC 3' (SEQ ID NO: 21)

for the GAPDH gene. Thirty two PCR cycles for ING1 and twenty two PCR cycles for GAPDH were performed using standard conditions [17]. Primers for GAPDH were added to PCR tubes at the end of the 10th cycle [27].

The levels of ING1 mRNA were estimated by scanning densitometry to be approximately ten fold higher in senescent fibroblasts compared to young fibroblasts. In order to see if increased mRNA levels resulted in increased protein levels, Western blotting experiments were performed with a rabbit polyclonal antibody that was raised against a bacterially expressed glutathione-S-transferase (GST)-p33$^{ING1}$ fusion protein and that reacted with a 33 kDa protein in human and mouse cell lysates.

Hs68 and NMuMG cells were harvested and 20 μg of total protein was used in each lane. Proteins were separated by electrophoresis in 12.5% polyacrylamide/SDS gels, and transferred to membranes for 1 hour using an electroblotter. The membranes were blocked in TBS(100 mM Tris, 150 mM NaCl) containing 10% nonfat dried milk and 0.1% Tween-20 for 2 hours. Incubation of the membranes with p33$^{ING1}$ antiserum was performed in TBS containing 5% nonfat milk and 0.1% Tween-20 for 1 hour and then membranes were washed with TBST solution for 30 minutes. Horseradish peroxidase-conjugated goat anti-rabbit antibody was then applied to the filters for 1 hour in TBST. Peroxidase activity was detected using ECL (Amersham Canada, Oakville, Ontario, Canada) and relative band intensities were determined by scanning densitometry.

As shown in FIG. 8B, the level of p33$^{ING1}$ protein increases approximately 8 fold when cells approach the end of their in vitro replicative lifespan, consistent with results obtained using RT-PCR.

Since ING1 appears to arrest cells in G1 when overexpressed and senescent cells are primarily arrested in the G1 phase of the cell cycle [28], the level of p33$^{ING1}$ protein was tested during the cell cycle. Quiescent, proliferation-competent NMuMG cells were serum stimulated, lysates were prepared at different times after serum addition, and samples were analyzed by Western blotting with anti-p33 antibodies by the method set forth above. The level of p33$^{ING1}$ was found to decrease as cells exited from G0, to increase during late G1 and to reach a maximum in S phase. This was followed by a decrease in G2 of the cell cycle (FIG. 9B). CDK2 expression was used as a control for cell cycle progression and changed as reported previously (FIG. 9A) [29]. FIG. 9C shows the results of DNA content analysis by fluorescence-activated cell sorting (FACS) in parallel cultures indicating that cells enter S phase at 16 hours under these experimental conditions. These results indicate that ING1 is regulated following mitogen addition to quiescent cells, with expression reaching a peak during DNA synthesis.

To determine the effects of reducing the levels of ING1 mRNA on the replicative lifespan of HDFs, cells were infected with a pLNCX-αS (the construct carrying a 182 bp fragment in the antisense orientation and representing nucleotides 942 to 1,124 of the ING1 cDNA (FIG. 3)). This antisense fragment effectively inhibits translation of ING1 mRNA as shown previously where chronic expression of the antisense construct resulted in 90% inhibition of the expression of the endogenous p33$^{ING1}$ protein in cells.

Amphotropic and ecotropic packaging cells that were used for infection are capable of producing retroviruses with titers higher than $10^6$ per ml upon transient transfection which allows delivery of the retroviral construct to HDFs with efficiencies of approximately 90% as monitored by expression from a retroviral –β-galactosidase construct.

"Young" HDFs at 30 MPDs were "pre-aged" by continuous subculturing until reaching 70 MPDs. Hs68 cells at 70 mean population doublings (MPDs) were infected with the retroviral vector pLNCX as a control or with pLNCX-αS and were subcultured in parallel using subculturing ratios of 1:2. Infected cells were propagated an additional 10 MPDs after which $10^5$ control pLCNX and $10^5$ pLCNX-αS cells at 80 MPD were split into twelve 10 cm plates and cultivated for two months, with weekly refeeding using complete medium. Some of the cells infected with retrovirus alone were observed to divide once during this time, while cells containing the ING1-αS fragment continued to grow and created visible colonies.

To confirm the effect of the antisense fragment of ING1 in cells, indirect immunofluorescence with a rabbit polyclonal antibody that was raised against p33$^{ING1}$ was performed. Senescent vector-infected fibroblasts and fibroblasts from colonies resulting from ING1-αS retrovirus infection were grown on glass coverslips for 48 hours at 37° C. to 60% confluence. Then the cells were fixed in 3.7% formaldehyde, washed in 0.5% Triton X100 and in 0.05% Tween 20 in PBS solution for 10 minutes each at room temperature. The cells were incubated with a 1:100 dilution of rabbit p33$^{ING1}$ antiserum for 30 min, washed in PBS with 0.05% Tween, incubated with goat anti-rabbit IgG-biotin antibody and then with streptavidin conjugated Texas Red. Samples were examined with a Zeiss Axiophot fluorescence microscope and images were photographed on Kodak TMAX 400 film.

Staining with anti-p33 antibody was observed in the nuclear compartment of senescent cells containing control virus but not in cells obtained from colonies that had received antisense p33 retrovirus. These results corroborate the previous observations that p33$^{ING1}$ is a nuclear protein and confirmed that the levels of p33$^{ING1}$ protein decrease in cells from colonies resulting from ING1-αS retrovirus infection. Similar results were seen in cells from 3 individual colonies and from 20 independent senescent cells containing control retrovirus.

Figure 10:
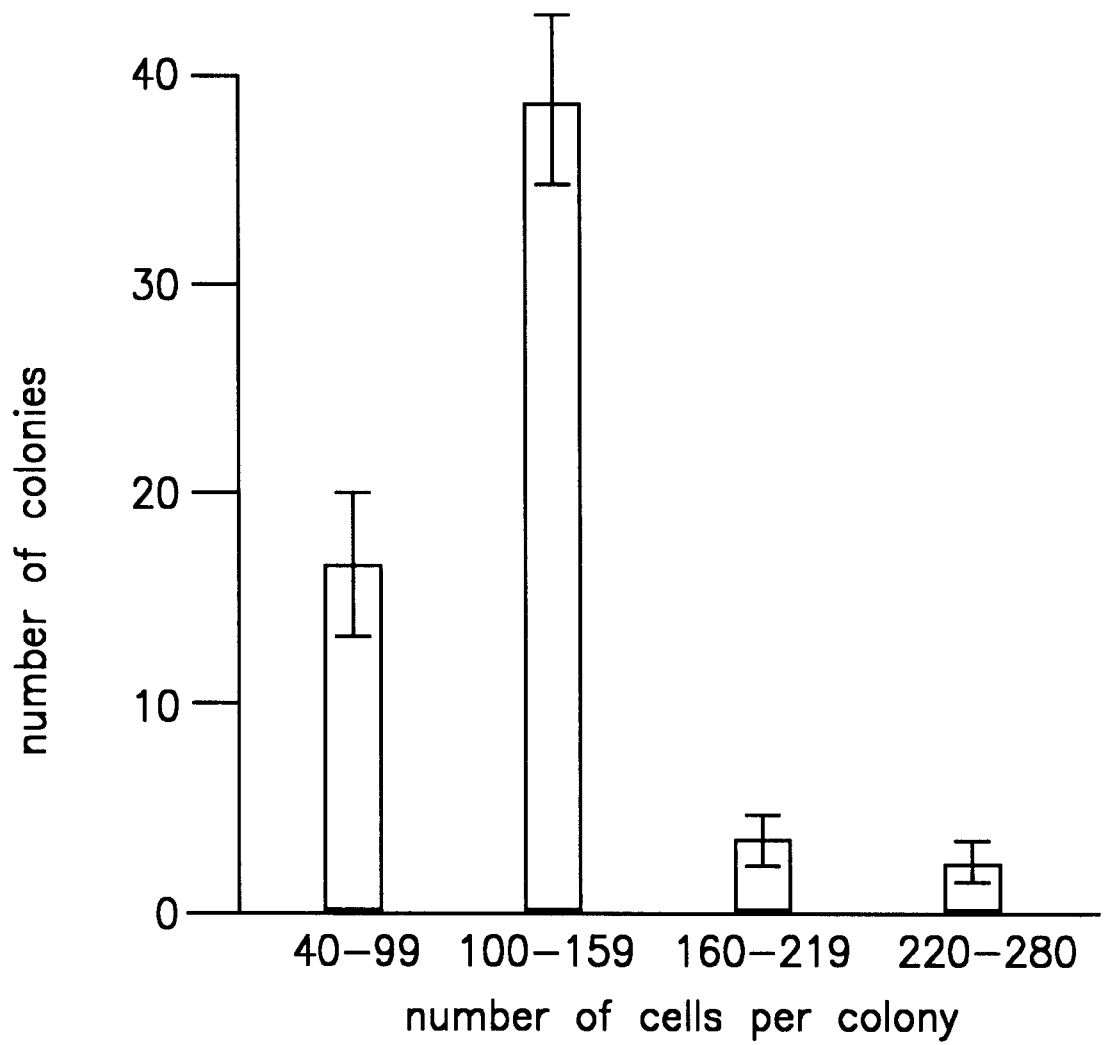
FIG. 10 illustrates the number of cells per colony of cells blocked for ING1 expression.

To estimate the efficiency with which down regulation of the ING1 gene by infection with PLCNX-αS was able to extend the proliferative lifespan of normal fibroblasts, the number of cells in each colony was counted. Results of these calculations are shown in FIG. 10 in which colonies were divided into 4 groups depending upon the number of cells in the colony. Most colonies contained 100–159 cells, therefore if cells divided in an arithmetic progression (2,4,8 . . . n) this class corresponds to approximately 7 additional MPDs ($2^7$=128). Colonies in the largest category (220–280) correspond to 8 cell doublings ($2^8$=256). Similar results were obtained in two separate trials and strongly indicate that down regulation of p33$^{ING1}$ protein is sufficient to extend the proliferative lifespan of normal fibroblasts by approximately 10%, as previously reported for the p53 tumor suppressor gene [30].

Example 10

Figure 11A:
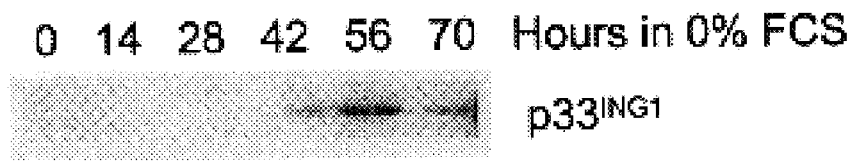
FIGS. 11A–11B illustrate that ING1 protein levels increase during serum starvation-induced apoptosis of P19 teratocarcinoma cells.

Indications that ING1 may be involved in the modulation of apoptosis first came from the conspicuous presence of ING1 in regressing tail and absence from growing hindlimbs of metamorphosing Xenopus tadpoles and second, the serum deprivation-induced elevation of ING1 levels in P19 teratocarcinoma cells that correlated with the induction of apoptosis within 48–72 hours (FIG. 11A; 35).

In order to establish the effect of ING1 expression on apoptosis, we infected P19 cells with sense (S), antisense (aS) and retroviral vector alone (V) and examined cell viability 72 hours after serum withdrawal.

P19 mouse teratocarcinoma cells were grown in alpha MEM medium with 10% fetal calf serum (FCS: GIBCO/BRL, Burlington, Ontario, CANADA). For serum starvation experiments, the cells were washed twice in PBS (phosphate buffered saline; 137 mM NaCl, 2.7 mM KCl, 10.1 mM Na$_2$HPO$_4$, 1.8 mM KH$_2$PO$_4$, pH 7.4) and serum-free alpha MEM (GIBCO/BRL) was added.

Retroviral infection of target cells was used to introduce ING1 expression constructs. Because the ING1 protein appears to block entry into S-phase of the cell cycle the use of standard drug resistance selection methods is precluded. Retroviral infection also has a higher efficiency than standard calcium phosphate transfection procedures. The retroviral vector, pLNCX (7), containing sense (S), antisense (aS; nucleotides 942 to 1124 of the ING1 cDNA) or vector alone were transfected into a highly-efficient BOSC23 ecotropic virus-packaging cell line. The BOSC23 supernatant was then used to infect ecotropic producer cell lines. The target P19 cells were plated at $10^4$ cells per 10 cm plate and infected with undiluted viral supernatant from ecotropic producer cells. Infection efficiency was determined to be about 60% with the P19 cells because these cells were prone to clumping.

Cell viability was assessed using a trypan blue dye exclusion assay. Cell suspensions were mixed 4:1 with 0.5% trypan blue:saline solution (GIBCO/BRL). The cells were incubated at room temperature for 5 minutes and counted with a hemacytometer.

Figure 11B:
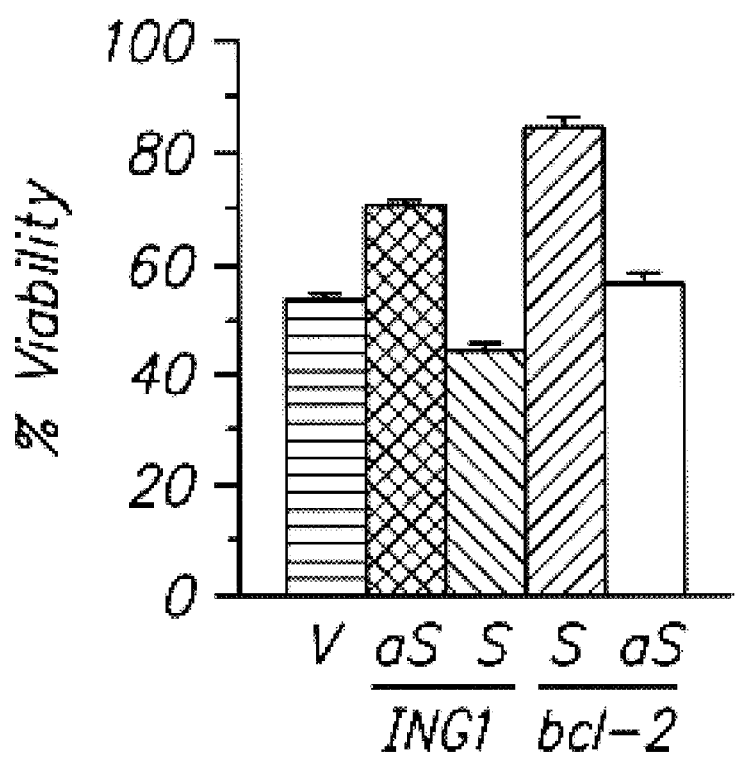

As shown in FIG. 11B, the antisense ING1 construct conferred a moderate level of protection against death (70% viable) compared to that conferred by a retroviral construct constitutively expressing the bcl-2 gene (84% viable). Conversely, P19 cells expressing the sense ING1 construct exhibited greater death (44% viable) than the vector only (54% viable) or antisense bcl-2 controls (56% viable), suggesting that ING1 confers cellular susceptibility to death induced by serum starvation. These numbers represent a minimal estimate of the effects of ING1 and bcl-2 due to the modest transfection efficiency of P19 cells as outlined above.

Since the infection efficiency was low for P19 cells, we turned to another model system of apoptosis developed in our laboratory, that of rodent fibroblasts (Rat 1 and NIH 3T3) containing a tetracycline-controlled human c-myc gene (tet-myc cells). Because these cells form a monolayer, transfection efficiencies of greater than 90% are obtainable.

The human c-myc gene was inserted into a plasmid containing a minimal cytomegalovirus promoter preceded by several binding sites for the tetracycline transcriptional protein (TA) (36). This construct (hTIC-myc) was stably transfected into NIH3T3 or Rat1 cells previously selected for the stable expression of the TA protein that is capable of binding to, and activating transcription of the myc gene on the hTIC-myc construct, in the absence of tetracycline. In the presence of tetracycline, the TA protein is blocked from binding and very little, if any transcription is seen from the c-myc expression construct. If tetracycline is washed from the cells, expression of the c-myc gene increases and expression can be regulated by altering the level of tetracycline to give up to 100 fold higher expression levels. Transformed cell lines that showed low background expression of c-myc and a high degree of inducibility were chosen for future studies.

The transformed rodent fibroblasts, either NIH 3T3- or rat 1-derived cells containing the tetracycline-controlled human c-myc gene (tet-myc cells) were maintained in high glucose Dulbecco's MEM (GIBCO/BRL) supplemented with 10% FCS and 2 μg/ml tetracycline (Sigma, St. Louis, Mo.) to repress premature human c-myc gene repression. Removal of tetracycline from the medium results in the rapid accumulation of human c-myc protein (FIG. 12A) and subsequent apoptosis. The advantage of such a system is that control and experimental cells possess an identical genetic background and the potential for cellular adaptation to constitutive c-myc overexpression is minimized.

The tet-myc NIH3T3 or Rat1 cells were plated at $10^4$ cells per 10 cm plate and infected with undiluted viral supernatant from ecotropic BOSC23 cells described above. Infection efficiency was determined to be greater than 90% for NIH 3T3 tet-myc cells using a retroviral β-galactosidase construct.

Tet-myc cells containing the retroviral constructs were seeded at a density of approximately $10^4$ cells/cm$^2$ on glass coverslips and grown at 37° C. for 48 hours before processing as described (16).

The cells were subsequently treated to induce c-myc expression and apoptosis. Briefly, this involved washing out the tetracycline inhibitor, elevating c-myc expression by up to 100 fold, and then transferring cells to medium without serum where apoptosis rapidly ensued. Nuclear proteins were isolated at certain timepoints and immunoblotted.

DNA laddering was assessed using the method of Smith et al (32). Tet-myc cells were plated at equal densities as described above. At 72 hours after exposure to 0.1% FCS, DNA was isolated from the floating cells on a per plate basis. Equal volumes of lysate were run on a 2% agarose gel and stained with ethidium bromide.

Figure 13B:
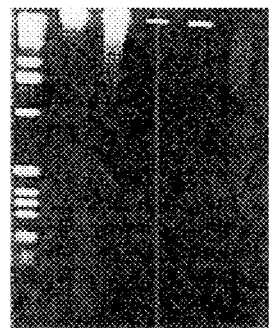
Figure 13C:
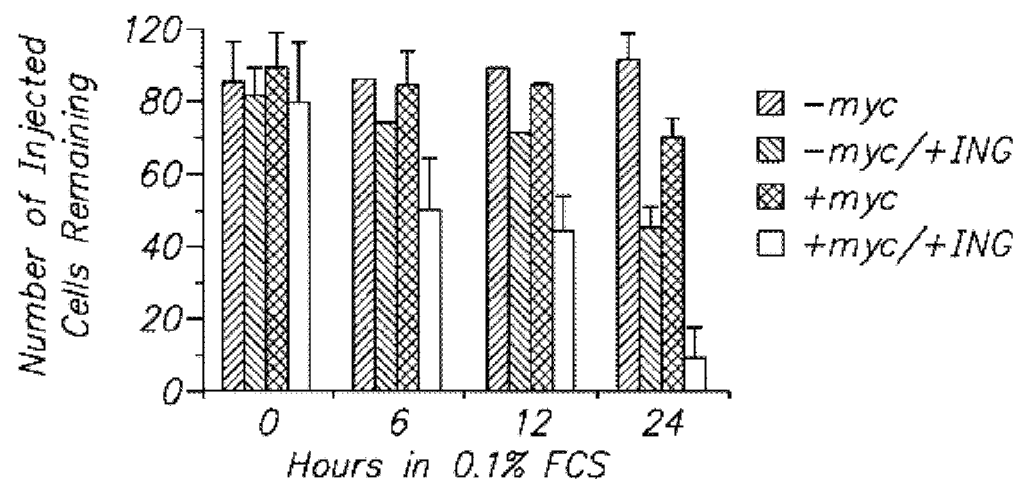

When c-myc was induced in the NIH 3T3 tet-myc cells by tetracycline withdrawal and the cells were then serum starved for 72 hours, they showed a viability of 65% compared with controls where c-myc was not induced (FIG. 13A). Apoptosis was minimized in cells coexpressing the antisense ING1 construct with only 5% of cells dying upon serum withdrawal. Cells expressing ING1 protein alone showed 70% viability after serum starvation and apoptosis. This was magnified when both the ING1 and the c-myc gene were coexpressed (40% viability). These cells exhibited several hallmarks of apoptosis including shrinkage, loss of substrate adhesion and chromatin condensation. In addition, internucleosomal DNA fragmentation was greatly enhanced in tet-myc cells expressing p33$^{ING1}$ compared to vector only, antisense ING1 or bcl-2-expressing tetmyc cells (FIG. 13B).

To confirm that ING1 enhances apoptosis during serum starvation, we microinjected p33$^{ING1}$ or a CMV-ING1 expression constructs into rat tet-myc fibroblasts and counted the number of remaining injected cells at various times after serum deprivation. Rat tet-myc cells were seeded on coverslips as described above and injected with about 25 μg/ml of GST-ING1 protein or GST protein, or with 25 μg/ml of CMV-driven ING1 expression construct or vector alone (31). After allowing the cells to recover for 4–6 hours, the coverslips were washed twice with PBS and the cells were serum starved. Injected cells were identified through coinjection and subsequent immunostaining of a coinjected nonspecific antibody. Because the history of each injected cell could be followed, a more dramatic effect of ING1 expression compared to the previous experimental approaches was apparent (45% viable at 24 h), with a further decrease in surviving cells when c-myc and ING1 were coexpressed (9% viable at 24 h). The results of the microinjection of the GST-ING1 protein are shown in FIG. 13A. Similar results were obtained with microinjection of the CMV-ING1 construct. These results support the data obtained with both the P19 and transformed NIH3T3 tet-myc cells and show that p33$^{ING1}$ is involved in regulation of apoptosis, in a manner that is synergistic with the action of c-myc.

It therefore appears that in at least three independent cell lines, ING1 expression confers an increased susceptibility to death upon serum starvation. Conversely, decreasing endogenous ING1 levels afforded some protection against cell death. ING1 markedly influences the outcome of c-myc-induced apoptosis and may, therefore, participate in guiding the response pathway whereby c-myc overexpression activates either apoptosis or tumorigenesis.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

What is claimed is:

1. A method to potentiate apoptosis in a eukaryotic cell, which method comprises:

a) selecting said eukaryotic cell; and b) increasing the $p33^{ING1}$ biological activity in said eukaryotic cell by introducing into said eukaryotic cell in vitro an effective amount of a peptide substantially identical to $p33^{ING1}$ and having $p33^{ING1}$ biological activity or an oligonucleotide which codes for a peptide substantially identical to $p33^{ING1}$ and having $p33^{ING1}$ biological activity under conditions such that apoptosis is potentiated.

2. The method of claim 1 wherein the $p33^{ING1}$ biological activity in said eukaryotic cell is increased by introducing into said eukaryotic cell an effective amount of a peptide substantially identical to $p33^{ING1}$ and having $p33^{ING1}$ biological activity.

3. The method of claim 1 wherein the $p33^{ING1}$ biological activity in said eukaryotic cell is increased by introducing into said eukaryotic cell an effective amount of an oligonucleotide which codes for a peptide substantially identical to $p33^{ING1}$ and having $p33^{ING1}$ biological activity under conditions such that a peptide comprising $p33^{ING1}$ biological activity is expressed.

4. The method of claim 1 wherein said eukaryotic cell is a mammalian cell.

5. The method of claim 4 wherein said mammalian cell is selected from the group consisting of normal cells and cancerous cells.

6. The method of claim 2 wherein the peptide comprises an amino acid sequence encoded by a nucleotide molecule comprising the DNA sequence of SEQ ID NO:1.

7. The method of claim 2 wherein the peptide comprises an amino acid sequence encoded by a nucleotide molecule comprising the DNA sequence of SEQ ID NO:9.

8. The method of claim 2 wherein the peptide comprises an amino acid sequence encoded by a a nucleotide molecule that hybridizes to the DNA molecule of SEQ ID NO:1 or SEQ ID NO:9, or the complements thereof, at a stringency equivalent to 0.1 times SSC, 0.1% SDS at 65° C.

9. The method of claim 3 wherein the oligonucleotide comprises the DNA sequence of SEQ ID NO:1.

10. The method of claim 3 wherein the oligonucleotide comprises the DNA sequence of SEQ ID NO:9.

11. The method of claim 3 wherein the oligonucleotide comprises a nucleotide molecule that hybridizes to the DNA molecule of SEQ ID NO:1 or SEQ ID NO:9 or the complements thereof, at a stringency equivalent to 0.1 times SSC, 0.1% SDS at 65° C.

* * * * *

```
                           SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 1902 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 109..741

(xi) SEQUENCE DESCRIPTION: SEQ ID NO:1:

CTGACCCGAG GGTGGGGCCG CGCGTGGCCG TGGAAACAGA TCCTGAAGGA GCTAGACGAG      60

TGCTACGAGC GCTTCAGTCG CGAGACAGAC GGGGCGCAGA AGCGGCGG ATG CTG CAC     117
                                                   Met Leu His
                                                     1

TGT GTG CAG CGC GCG CTG ATC CGC AGC CAG GAG CTG GGC GAC GAG AAG     165
Cys Val Gln Arg Ala Leu Ile Arg Ser Gln Glu Leu Gly Asp Glu Lys
        5                  10                  15

ATC CAG ATC GTG AGC CAG ATG GTG GAG CTG GTG GAG AAC CGC ACG CGG     213
Ile Gln Ile Val Ser Gln Met Val Glu Leu Val Glu Asn Arg Thr Arg
 20                  25                  30                  35

CAG GTG GAC AGC CAC GTG GAG CTG TTC GAG GCG CAG CAG GAG CTG GGC     261
Gln Val Asp Ser His Val Glu Leu Phe Glu Ala Gln Gln Glu Leu Gly
                 40                  45                  50

GAC ACA GTG GGC AAC AGC GGC AAG GTT GGC GCG GAC AGG CCC AAT GGC     309
Asp Thr Val Gly Asn Ser Gly Lys Val Gly Ala Asp Arg Pro Asn Gly
             55                  60                  65

GAT GCG GTA GCG CAG TCT GAC AAG CCC AAC AGC AAG CGC TCA CGG CGG     357
Asp Ala Val Ala Gln Ser Asp Lys Pro Asn Ser Lys Arg Ser Arg Arg
         70                  75                  80

CAG CGC AAC AAC GAG AAC CGT GAG AAC GCG TCC AGC AAC CAC GAC CAC     405
Gln Arg Asn Asn Glu Asn Arg Glu Asn Ala Ser Ser Asn His Asp His
 85                  90                  95

GAC GAC GGC GCC TCG GGC ACA CCC AAG GAG AAG AAG GCC AAG ACC TCC     453
Asp Asp Gly Ala Ser Gly Thr Pro Lys Glu Lys Lys Ala Lys Thr Ser
100                 105                 110                 115

AAG AAG AAG AAG CGC TCC AAG GCC AAG GCG GAG CGA GAG GCG TCC CCT     501
Lys Lys Lys Lys Arg Ser Lys Ala Lys Ala Glu Arg Glu Ala Ser Pro
                120                 125                 130

GCC GAC CTC CCC ATC GAC CCC AAC GAA CCC ACG TAC TGT CTG TGC AAC     549
Ala Asp Leu Pro Ile Asp Pro Asn Glu Pro Thr Tyr Cys Leu Cys Asn
            135                 140                 145

CAG GTC TCC TAT GGG GAG ATG ATC GGC TGC GAC AAC GAC GAG TGC CCC     597
Gln Val Ser Tyr Gly Glu Met Ile Gly Cys Asp Asn Asp Glu Cys Pro
        150                 155                 160
```

```
ATC GAG TGG TTC CAC TTC TCG TGC GTG GGG CTC AAT CAT AAA CCC AAG      645
Ile Glu Trp Phe His Phe Ser Cys Val Gly Leu Asn His Lys Pro Lys
    165                 170                 175

GGC AAG TGG TAC TGT CCC AAG TGC CGG GGG GAG AAC GAG AAG ACC ATG      693
Gly Lys Trp Tyr Cys Pro Lys Cys Arg Gly Glu Asn Glu Lys Thr Met
180                 185                 190                 195

GAC AAA GCC CTG GAG AAA TCC AAA AAA GAG AGG GCT TAC AAC AGG TAG      741
Asp Lys Ala Leu Glu Lys Ser Lys Lys Glu Arg Ala Tyr Asn Arg *
                200                 205                 210

TTTGTGGACA GGCGCCTGGT GTGAGGAGGA CAAAATAAAC CGTGTATTTA TTACATTGCT    801

GCCTTTGTTG AGGTGCAAGG AGTGTAAAAT GTATATTTTT AAAGAATGTT AGAAAAGGAA    861

CCATTCCTTT CATAGGGATG GCAGTGATTC TGTTTGCCTT TTGTTTTCAT GGTACACGT     921

GTAACAAGAA AGTGGTCTGT GGATCAGCAT TTTAGAAACT ACAAATATAG GTTTGATTCA    981

ACACTTAAGT CTCAGACTGA TTTCTTGCGG GAGGAGGGGG ACTAAACTCA CCCTAACACA   1041

TTAAATGTGG AAGGAAAATA TTTCATTAGC TTTTTTATTT TAATACAAGT AATATTATTA   1101

CTTTATGAAC AATTTTTTTT AATTGGCCAT GTCGCCAAAA ATACAGCCTA TAGTAAATGT   1161

GTTTCTTGCT GCCATGATGT ATATCCATAT AACAATTCAG TAACAAAGGT TTAAAGTTTG   1221

AAGATTATTT TTTAAAAAGG TAAAAGGTTA AATTTTACAT GACAGATATT TTATCTATTG   1281

GCCTGTTCCC CAAATGGCCA TTTTAAAATG CTTGGGTACA CTTCTCTTAA GTGGTCTAGT   1341

CAAGGAACCT CAAGTCATGC TTTTGCTATC ACCAATCATA GTGTACCCAT CTTTAATTTA   1401

TATCAGGTGT ATAAATGTAC ATTTCCAAAT GAACTTGCAC TGTAATATTA TAATTGGAAG   1461

TGCAGTCAGC AGTAGCTGTC GGAGCTAATG TCACAATTAT GTGCAAAGGT GTGCTTCCTG   1521

CTGTATGTGA GCTGTAAAAA TGTTACGTGA AGAAATAAAT GAAACTTGGC CAGTTTGTTC   1581

CTCTAGTAGT ATATTTAATT TTGACATAAG TAACTTTTAA AATTTGTCTT AAAAATTTAT   1641

ACACCAGCAA TTTAGACAAA GCCTTAAGCA AATTTTGTAT TATTGTTCTC ACTTATTATT   1701

AATAATGAAG TAGAAGTTAC TTAATTGCCA GCAAATAAAT ACGTGTCAAA AAGAATCTG    1761

TATTCAGACC CCTGGGGTCA GGAAATTACT GCCCCACTTG TCAAGTTCAG CCCACCATCT   1821

GTTTGAACAT TATATGAAGT TTAAATTCTA GTGTCCATAA ATAAAGTTTC AGCGGCACCC   1881

CAAAAAAAAA AAAAAAAAA A                                             1902

(2) INFORMATION FOR SEQ ID NO:2:

(i) SEQUENCE CHARACTERISTICS:
        (A) LENGTH:  210 amino acids
        (B) TYPE:  amino acid
        (D) TOPOLOGY:  linear (ii) MOLECULE TYPE:  protein (xi) SEQUENCE DESCRIPTION: SEQ ID NO:2:

Met Leu His Cys Val Gln Arg Ala Leu Ile Arg Ser Gln Glu Leu Gly
1                5                  10                  15

Asp Glu Lys Ile Gln Ile Val Ser Gln Met Val Glu Leu Val Glu Asn
                20                  25                  30

Arg Thr Arg Gln Val Asp Ser His Val Glu Leu Phe Glu Ala Gln Gln
            35                  40                  45

Glu Leu Gly Asp Thr Val Gly Asn Ser Gly Lys Val Gly Ala Asp Arg
        50                  55                  60

Pro Asn Gly Asp Ala Val Ala Gln Ser Asp Lys Pro Asn Ser Lys Arg
65                  70                  75                  80
```

```
Ser Arg Arg Gln Arg Asn Asn Glu Asn Arg Glu Asn Ala Ser Ser Asn
             85                  90                  95

His Asp His Asp Asp Gly Ala Ser Gly Thr Pro Lys Glu Lys Lys Ala
            100                 105                 110

Lys Thr Ser Lys Lys Lys Arg Ser Lys Ala Lys Ala Glu Arg Glu
            115                 120                 125

Ala Ser Pro Ala Asp Leu Pro Ile Asp Pro Asn Glu Pro Thr Tyr Cys
        130                 135                 140

Leu Cys Asn Gln Val Ser Tyr Gly Glu Met Ile Gly Cys Asp Asn Asp
145                 150                 155                 160

Glu Cys Pro Ile Glu Trp Phe His Phe Ser Cys Val Gly Leu Asn His
                165                 170                 175

Lys Pro Lys Gly Lys Trp Tyr Cys Pro Lys Cys Arg Gly Glu Asn Glu
            180                 185                 190

Lys Thr Met Asp Lys Ala Leu Glu Lys Ser Lys Lys Glu Arg Ala Tyr
        195                 200                 205

Asn Arg *
    210

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

GACCTGGCTC TAGAATTCAC GACA                                              24

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GATCTGTCGT GAATTCTAGA GCCAGG                                            26

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

GACTCGACGT TGTAACACGG CAGT                                              24

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
```

(D) TOPOLOGY: linear (ii) MOLECULE TYPE: other nucleic acid (xi) SEQUENCE DESCRIPTION: SEQ ID NO:6:

GATCACTGCC GTGTTACAAC GTCGAG                                          26

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

CCAAGCTTTG TTTACATCGA TGGATG                                          26

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

ATGGCGTTAA CTTAAGCTAG CTTGCCAAAC CTAC                                 34

(2) INFORMATION FOR SEQ ID NO:9:

(i) SEQUENCE CHARACTERISTICS:
        (A) LENGTH: 2061 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 16..900

(xi) SEQUENCE DESCRIPTION: SEQ ID NO:9:

GAGTAACCCG ATAAT ATG CCG TTG TGC ACG GCG ACG AGA ATT CCC AGA TAT      51
              Met Pro Leu Cys Thr Ala Thr Arg Ile Pro Arg Tyr
                  215                 220

AGC AGT AGC AGT GAT CCC GGG CCT GTG GCT CGG GGC CGG GGC TGC AGT       99
Ser Ser Ser Ser Asp Pro Gly Pro Val Ala Arg Gly Arg Gly Cys Ser
225                 230                 235

TCG GAC CGC CTC CCG CGA CCC GCG GGG CCG GCT CGG AGA CAG TTT CAG      147
Ser Asp Arg Leu Pro Arg Pro Ala Gly Pro Ala Arg Arg Gln Phe Gln
240                 245                 250                 255

GCC GCA TCT TTG CTG ACC CGA GGG TGG GGC CGC GCG TGG CCG TGG AAA      195
Ala Ala Ser Leu Leu Thr Arg Gly Trp Gly Arg Ala Trp Pro Trp Lys
                260                 265                 270

CAG ATC CTG AAG GAG CTA GAC GAG TGC TAC GAG CGC TTC AGT CGC GAG      243
Gln Ile Leu Lys Glu Leu Asp Glu Cys Tyr Glu Arg Phe Ser Arg Glu
    275                 280                 285

ACA GAC GGG GCG CAG AAG CGG CGG ATG CTG CAC TGT GTG CAG CGC GCG      291
Thr Asp Gly Ala Gln Lys Arg Arg Met Leu His Cys Val Gln Arg Ala
290                 295                 300

```
CTG ATC CGC AGC CAG GAG CTG GGC GAC GAG AAG ATC CAG ATC GTG AGC      339
Leu Ile Arg Ser Gln Glu Leu Gly Asp Glu Lys Ile Gln Ile Val Ser
    305                 310                 315

CAG ATG GTG GAG CTG GTG GAG AAC CGC ACG CGG CAG GTG GAC AGC CAC      387
Gln Met Val Glu Leu Val Glu Asn Arg Thr Arg Gln Val Asp Ser His
320                 325                 330                 335

GTG GAG CTG TTC GAG GCG CAG CAG GAG CTG GGC GAC ACA GTG GGC AAC      435
Val Glu Leu Phe Glu Ala Gln Gln Glu Leu Gly Asp Thr Val Gly Asn
                340                 345                 350

AGC GGC AAG GTT GGC GCG GAC AGG CCC AAT GGC GAT GCG GTA GCG CAG      483
Ser Gly Lys Val Gly Ala Asp Arg Pro Asn Gly Asp Ala Val Ala Gln
            355                 360                 365

TCT GAC AAG CCC AAC AGC AAG CGC TCA CGG CGG CAG CGC AAC AAC GAG      531
Ser Asp Lys Pro Asn Ser Lys Arg Ser Arg Arg Gln Arg Asn Asn Glu
        370                 375                 380

AAC CGT GAG AAC GCG TCC AGC AAC CAC GAC CAC GAC GAC GGC GCC TCG      579
Asn Arg Glu Asn Ala Ser Ser Asn His Asp His Asp Asp Gly Ala Ser
    385                 390                 395

GGC ACA CCC AAG GAG AAG AAG GCC AAG ACC TCC AAG AAG AAG AAG CGC      627
Gly Thr Pro Lys Glu Lys Lys Ala Lys Thr Ser Lys Lys Lys Lys Arg
400                 405                 410                 415

TCC AAG GCC AAG GCG GAG CGA GAG GCG TCC CCT GCC GAC CTC CCC ATC      675
Ser Lys Ala Lys Ala Glu Arg Glu Ala Ser Pro Ala Asp Leu Pro Ile
                420                 425                 430

GAC CCC AAC GAA CCC ACG TAC TGT CTG TGC AAC CAG GTC TCC TAT GGG      723
Asp Pro Asn Glu Pro Thr Tyr Cys Leu Cys Asn Gln Val Ser Tyr Gly
            435                 440                 445

GAG ATG ATC GGC TGC GAC AAC GAC GAG TGC CCC ATC GAG TGG TTC CAC      771
Glu Met Ile Gly Cys Asp Asn Asp Glu Cys Pro Ile Glu Trp Phe His
        450                 455                 460

TTC TCG TGC GTG GGG CTC AAT CAT AAA CCC AAG GGC AAG TGG TAC TGT      819
Phe Ser Cys Val Gly Leu Asn His Lys Pro Lys Gly Lys Trp Tyr Cys
    465                 470                 475

CCC AAG TGC CGG GGG GAG AAC GAG AAG ACC ATG GAC AAA GCC CTG GAG      867
Pro Lys Cys Arg Gly Glu Asn Glu Lys Thr Met Asp Lys Ala Leu Glu
480                 485                 490                 495

AAA TCC AAA AAA GAG AGG GCT TAC AAC AGG TAG TTTGTGGACA GGCGCCTGGT   920
Lys Ser Lys Lys Glu Arg Ala Tyr Asn Arg  *
                500                 505

GTGAGGAGGA CAAAATAAAC CGTGTATTTA TTACATTGCT GCCTTTGTTG AGGTGCAAGG    980

AGTGTAAAAT GTATATTTTT AAAGAATGTT AGAAAAGGAA CCATTCCTTT CATAGGGATG   1040

GCAGTGATTC TGTTTGCCTT TTGTTTTCAT TGGTACACGT GTAACAAGAA AGTGGTCTGT   1100

GGATCAGCAT TTTAGAAACT ACAAATATAG GTTTGATTCA ACACTTAAGT CTCAGACTGA   1160

TTTCTTGCGG GAGGAGGGGG ACTAAACTCA CCCTAACACA TTAAATGTGG AAGGAAAATA   1220

TTTCATTAGC TTTTTTATTT TAATACAAGT AATATTATTA CTTTATGAAC AATTTTTTTT   1280

AATTGGCCAT GTCGCCAAAA ATACAGCCTA TAGTAAATGT GTTTCTTGCT GCCATGATGT   1340

ATATCCATAT AACAATTCAG TAACAAAGGT TTAAAGTTTG AAGATTATTT TTAAAAAGG    1400

TAAAAGGTTA AATTTTACAT GACAGATATT TTATCTATTG GCCTGTTCCC CAAATGGCCA   1460

TTTTAAAATG CTTGGGTACA CTTCTCTTAA GTGGTCTAGT CAAGGAACCT CAAGTCATGC   1520

TTTTGCTATC ACCAATCATA GTGTACCCAT CTTTAATTTA TATCAGGTGT ATAAATGTAC   1580

ATTTCCAAAT GAACTTGCAC TGTAATATTA TAATTGGAAG TGCAGTCAGC AGTAGCTGTC   1640

GGAGCTAATG TCACAATTAT GTGCAAAGGT GTGCTTCCTG CTGTATGTGA GCTGTAAAAA   1700

TGTTACGTGA AGAAATAAAT GAAACTTGGC CAGTTTGTTC CTCTAGTAGT ATATTTAATT   1760
```

```
TTGACATAAG TAACTTTTAA AATTTGTCTT AAAAATTTAT ACACCAGCAA TTTAGACAAA    1820

GCCTTAAGCA AATTTTGTAT TATTGTTCTC ACTTATTATT AATAATGAAG TAGAAGTTAC    1880

TTAATTGCCA GCAAATAAAT ACGTGTCAAA AAAGAATCTG TATTCAGACC CCTGGGGTCA    1940

GGAAATTACT GCCCCACTTG TCAAGTTCAG CCCACCATCT GTTTGAACAT TATATGAAGT    2000

TTAAATTCTA GTGTCCATAA ATAAAGTTTC AGCGGCACCC CAAAAAAAAA AAAAAAAAA     2060

A                                                                    2061
```

(2) INFORMATION FOR SEQ ID NO:10:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO:10:

```
Met Pro Leu Cys Thr Ala Thr Arg Ile Pro Arg Tyr Ser Ser Ser
 1               5                  10                  15

Asp Pro Gly Pro Val Ala Arg Gly Arg Gly Cys Ser Ser Asp Arg Leu
                 20                  25                  30

Pro Arg Pro Ala Gly Pro Ala Arg Arg Gln Phe Gln Ala Ala Ser Leu
             35                  40                  45

Leu Thr Arg Gly Trp Gly Arg Ala Trp Pro Trp Lys Gln Ile Leu Lys
         50                  55                  60

Glu Leu Asp Glu Cys Tyr Glu Arg Phe Ser Arg Glu Thr Asp Gly Ala
 65                  70                  75                  80

Gln Lys Arg Arg Met Leu His Cys Val Gln Arg Ala Leu Ile Arg Ser
                 85                  90                  95

Gln Glu Leu Gly Asp Glu Lys Ile Gln Ile Val Ser Gln Met Val Glu
                100                 105                 110

Leu Val Glu Asn Arg Thr Arg Gln Val Asp Ser His Val Glu Leu Phe
            115                 120                 125

Glu Ala Gln Gln Glu Leu Gly Asp Thr Val Gly Asn Ser Gly Lys Val
130                 135                 140

Gly Ala Asp Arg Pro Asn Gly Asp Ala Val Ala Gln Ser Asp Lys Pro
145                 150                 155                 160

Asn Ser Lys Arg Ser Arg Arg Gln Arg Asn Asn Glu Asn Arg Glu Asn
                165                 170                 175

Ala Ser Ser Asn His Asp His Asp Asp Gly Ala Ser Gly Thr Pro Lys
            180                 185                 190

Glu Lys Lys Ala Lys Thr Ser Lys Lys Lys Arg Ser Lys Ala Lys
                195                 200                 205

Ala Glu Arg Glu Ala Ser Pro Ala Asp Leu Pro Ile Asp Pro Asn Glu
210                 215                 220

Pro Thr Tyr Cys Leu Cys Asn Gln Val Ser Tyr Gly Glu Met Ile Gly
225                 230                 235                 240

Cys Asp Asn Asp Glu Cys Pro Ile Glu Trp Phe His Phe Ser Cys Val
                245                 250                 255

Gly Leu Asn His Lys Pro Lys Gly Lys Trp Tyr Cys Pro Lys Cys Arg
            260                 265                 270

Gly Glu Asn Glu Lys Thr Met Asp Lys Ala Leu Glu Lys Ser Lys Lys
            275                 280                 285
```

Glu Arg Ala Tyr Asn Arg
    290                 295

(2) INFORMATION FOR SEQ ID NO:11:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

GTACATATTG TCGTTAGAAC GCGTAATACG CCTCACTATA GGGA        44

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

CTGGATCTTC TCGTCGCC        18

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

AGTGCAGCAT CGGCCGCTTC        20

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

GTACATATTG TCGTTAGAAC GCG        23

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

TAATACGCCT CACTATAGGG A        21

-continued (2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

ACGCACGAGA AGTGGAACCA                                      20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

TTTGGATTTC TCCAGGGCTT                                      20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

TACCTGTTGT AAGCCCTCTC                                      20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

GAAGCGGCGG ATGCTGCACT                                      20

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CGGAGTCAAC GGATTTGGTC GTAT                                  24

(2) INFORMATION FOR SEQ ID NO:21:

(i) SEQUENCE CHARACTERISTICS:
        (A) LENGTH: 24 base pairs

```
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:21:

AGCCTTCTCC ATGGTGGTGA AGAC                                             24

(2) INFORMATION FOR SEQ ID NO:22:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:22:

AATCATCGAT GGATGGATGG                                                  20

(2) INFORMATION FOR SEQ ID NO:23:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:23:

CCATCCATCC ATCGATGATT AAA                                              23
```